(12) United States Patent
Zeldis et al.

(10) Patent No.: US 7,612,096 B2
(45) Date of Patent: Nov. 3, 2009

(54) METHODS FOR TREATMENT, MODIFICATION AND MANAGEMENT OF RADICULOPATHY USING 1-OXO-2-(2,6-DIOXOPIPERIDIN-3YL)-4-AMINOISOINDOLINE

(75) Inventors: Jerome B. Zeldis, Princeton, NJ (US); Herbert Faleck, West Orange, NJ (US); Donald C. Manning, Bloomsbury, NJ (US)

(73) Assignee: Celgene Corporation, Summit, NJ (US)

( * ) Notice: Subject to any disclaimer, the term of this patent is extended or adjusted under 35 U.S.C. 154(b) by 331 days.

(21) Appl. No.: 10/576,152

(22) PCT Filed: Apr. 23, 2004

(86) PCT No.: PCT/US2004/012721
§ 371 (c)(1),
(2), (4) Date: Feb. 13, 2007

(87) PCT Pub. No.: WO2005/044178
PCT Pub. Date: May 19, 2005

(65) Prior Publication Data
US 2007/0244078 A1 Oct. 18, 2007

(51) Int. Cl.
*A01N 43/40* (2006.01)
*A61K 31/445* (2006.01)

(52) U.S. Cl. .................. 514/323; 514/315; 514/317; 514/319; 514/320

(58) Field of Classification Search .................. None
See application file for complete search history.

(56) References Cited

U.S. PATENT DOCUMENTS

| | | | |
|---|---|---|---|
| 3,536,809 A | 10/1970 | Applezweig | |
| 3,598,123 A | 8/1971 | Zaffaroni | |
| 3,845,770 A | 11/1974 | Theeuwes et al. | |
| 3,916,899 A | 11/1975 | Theeuwes et al. | |
| 4,008,719 A | 2/1977 | Theeuwes et al. | |
| 4,215,114 A | 7/1980 | Szmuszkovicz et al. | |
| 5,059,595 A | 10/1991 | Le Grazie | |
| 5,073,543 A | 12/1991 | Marshall et al. | |
| 5,120,548 A | 6/1992 | McClelland et al. | |
| 5,134,127 A | 7/1992 | Stella et al. | |
| 5,354,556 A | 10/1994 | Sparks et al. | |
| 5,385,901 A | 1/1995 | Kaplan et al. | |
| 5,591,767 A | 1/1997 | Mohr et al. | |
| 5,593,990 A | 1/1997 | D'Amato | |
| 5,629,327 A | 5/1997 | D'Amato | |
| 5,635,517 A | 6/1997 | Muller et al. | |
| 5,639,476 A | 6/1997 | Oshlack et al. | |
| 5,674,533 A | 10/1997 | Santus et al. | |
| 5,698,579 A | 12/1997 | Muller | |
| 5,703,092 A | 12/1997 | Xue et al. | |
| 5,712,291 A | 1/1998 | D'Amato | |
| 5,733,566 A | 3/1998 | Lewis | |
| 5,798,368 A | 8/1998 | Muller et al. | |
| 5,874,448 A | 2/1999 | Muller et al. | |
| 5,877,200 A | 3/1999 | Muller | |
| 5,929,117 A | 7/1999 | Muller et al. | |
| 5,955,476 A | 9/1999 | Muller et al. | |
| 6,015,557 A | 1/2000 | Tobinick et al. | |
| 6,071,948 A | 6/2000 | D'Amato | |
| 6,177,077 B1 | 1/2001 | Tobinick | |
| 6,228,879 B1 | 5/2001 | Green et al. | |
| 6,281,230 B1 | 8/2001 | Muller et al. | |
| 6,316,471 B1 | 11/2001 | Muller et al. | |
| 6,335,349 B1 | 1/2002 | Muller et al. | |
| 6,379,666 B1 | 4/2002 | Tobinick | |
| 6,380,239 B1 | 4/2002 | Muller et al. | |
| 6,395,754 B1 | 5/2002 | Muller et al. | |
| 6,403,613 B1 * | 6/2002 | Man et al. ................... | 514/323 |
| 6,419,934 B1 | 7/2002 | Tobinick | |
| 6,419,944 B2 | 7/2002 | Tobinick | |
| 6,420,414 B1 | 7/2002 | D'Amato | |
| 6,423,321 B2 | 7/2002 | Tobinick | |
| 6,428,787 B1 | 8/2002 | Tobinick | |
| 6,458,810 B1 | 10/2002 | Muller et al. | |
| 6,469,045 B1 | 10/2002 | D'Amato | |
| 6,471,961 B1 | 10/2002 | Tobinick | |
| 6,476,052 B1 | 11/2002 | Muller et al. | |
| 6,537,549 B2 | 3/2003 | Tobinick | |
| 6,555,554 B2 | 4/2003 | Muller et al. | |

(Continued)

FOREIGN PATENT DOCUMENTS

WO  WO 98/03502  1/1998

(Continued)

OTHER PUBLICATIONS

Ignatowski et al. Brain Research (1999), vol. 841, pp. 70-77.*

(Continued)

*Primary Examiner*—Patrick T Lewis
(74) *Attorney, Agent, or Firm*—Jones Day

(57) ABSTRACT

Methods of treating, preventing, modifying and managing various types of pain are disclosed. Specific methods comprise the administration of an immunomodulatory compound, or a pharmaceutically acceptable salt, solvate, hydrate, stereoisomer, clathrate, or prodrug thereof, alone or in combination with a second active agent and/or surgery, psychological or physical therapy. Pharmaceutical compositions, single unit dosage forms, and kits suitable for use in methods of the invention are also disclosed.

17 Claims, No Drawings

U.S. PATENT DOCUMENTS

| | | |
|---|---|---|
| 6,623,736 B2 | 9/2003 | Tobinick |
| 6,635,250 B2 | 10/2003 | Olmarker et al. |
| 6,673,828 B1 | 1/2004 | Green et al. |
| 2001/0004456 A1 | 6/2001 | Tobinick |
| 2001/0016195 A1 | 8/2001 | Tobinick |
| 2001/0026801 A1 | 10/2001 | Tobinick |
| 2001/0056114 A1 | 12/2001 | D'Amato |
| 2002/0045643 A1 | 4/2002 | Muller et al. |
| 2002/0052398 A1 | 5/2002 | D'Amato |
| 2002/0054899 A1 | 5/2002 | D'Amato |
| 2002/0061923 A1 | 5/2002 | D'Amato |
| 2002/0131954 A1 | 9/2002 | Tobinick |
| 2002/0131955 A1 | 9/2002 | Tobinick |
| 2002/0161023 A1 | 10/2002 | D'Amato |
| 2002/0173658 A1 | 11/2002 | Muller et al. |
| 2002/0183360 A1 | 12/2002 | Muller et al. |
| 2003/0007972 A1 | 1/2003 | Tobinick |
| 2003/0028028 A1 | 2/2003 | Man et al. |
| 2003/0045552 A1 | 3/2003 | Robarge et al. |
| 2003/0049256 A1 | 3/2003 | Tobinick |
| 2003/0069428 A1 | 4/2003 | Muller et al. |
| 2003/0087962 A1 | 5/2003 | Demopulos et al. |
| 2003/0096841 A1 | 5/2003 | Robarge et al. |
| 2003/0113318 A1 | 6/2003 | Tobinick |
| 2003/0139451 A1 | 7/2003 | Shah et al. |
| 2003/0144325 A1 | 7/2003 | Muller et al. |
| 2003/0181428 A1 | 9/2003 | Green et al. |
| 2003/0185826 A1 | 10/2003 | Tobinick |
| 2003/0187024 A1 | 10/2003 | D'Amato |
| 2003/0191098 A1 | 10/2003 | D'Amato |
| 2003/0235909 A1 | 12/2003 | Hariri et al. |
| 2004/0029832 A1 | 2/2004 | Zeldi |
| 2004/0038874 A1 | 2/2004 | Omoigui |
| 2004/0077685 A1 | 4/2004 | Figg et al. |
| 2004/0077686 A1 | 4/2004 | Dannenberg et al. |
| 2004/0087546 A1 | 5/2004 | Zeldis |
| 2004/0091455 A1 | 5/2004 | Zeldis |
| 2004/0122052 A1 | 6/2004 | Muller et al. |

FOREIGN PATENT DOCUMENTS

| | | |
|---|---|---|
| WO | WO 98/54170 | 12/1998 |
| WO | WO 00/18409 | 4/2000 |
| WO | WO 02/059106 | 8/2002 |
| WO | WO03086373 | 10/2003 |

OTHER PUBLICATIONS

Laffitte et al. Exper. Opin. Drug Saf. (2004), vol. 3, pp. 47-56.*
Abbott, F. et al. *Pain* 60:91-102 (1995).
Arruda, Janice L. et al., *Brain Research*, 879, 216-225, 2000.
Bennett G J, *Clinical journal of pain*, 16(3 Suppl) S139-143, 2000.
Toussirot E., et al., *Expert opinion on investigational drugs*, 10(1), 21-9, Jan. 2001.
Carstensen, Jens T., *Drug Stability: Principles & Practice*, 2d. Ed., Marcel Dekker, NY, NY, 1995, pp. 379-380.
Corral, L.G. et al., Ann. Rheum. Dis. 58:(Suppl I) 1107-1113 (1999).
Dray, A., *British Journal of Anaesthesia*, 75: 125-131, 1995.
Dzwierzynski et al., *Hand Clinics* vol. 10 (1): 29-44 (1994).
Feng Huang, et al., *Arthritis and rheumatism*, 47(3), 249-54, Jun. 2002.
George, et al., *Pain*, 88, 267-275, 2000.
Hogan, Q., *Regional Anesthesia and Pain Medicine* 27(4):385-401 (2002).
Langerman et al., *Pharmacol. Toxicol. Methods* 34:23-27 (1995).
Malmberg, A. and Yaksh, T., *Pain* 60:83-90 (1995).
Miller, J.M., et al., *Antibiot. Med. Clin. Ther.*, 7, 743-746, 1960.
Perez R.S., et al., *J Pain Symptom Manage* Jun. 2001; 21(6): 511-26.
Rajkumar, S.V., et al., *Archives of internal medicine*, 161, 2502-3, Nov. 2001.
Schwartzman R.J., *N Engl J Med* 343(9): 654 (2000).
Schwartzman R.J., *Curr Opin Neural Neurosurg* 6(4): 531-6 (1993).
1 *Burger's Medicinal Chemistry and Drug Discovery*, 172-178, 949-982 (Manfred E. Wolff ed., 5th ed. 1995).
N. Ake Jonnson, 1972. "Chemical Structure and Teratogenic Properties," Acta Pharm., pp. 521-542.
Ji, 2003, "Activation of MAP kinases in primary sensory neurons," Proc. 10th World Congress on Pain, Prog. in Pain Res. and Management vol. 24, Ch. 8, pp. 81-87.
Kenney et al., 1998, "Peripheral axotomy induces long-term c-Jun amino-terminal kinase-I activation and activator protein-I binding activity by c-Jun and junD in adult rat dorsal root ganglia In vivo," J. Neurosci. 18(4):1318-1328.
Ma et al., 2002, "Partial sciatic nerve ligation induces increase in the phosphorylation of extracellular signal-regulated kinase (ERK) and c-Jun N-terminal kinase (JNK) in astrocytes in the lumbar spinal dorsal horn and the gracile nucleus," Pain 99(1-2):175-184.
Wagner et al., "Edoneurial injection of TNF-alpha produces neuropathic pain behaviors," Neuroreport, Nov. 25, 1996;7(18):2897-901.

* cited by examiner

METHODS FOR TREATMENT, MODIFICATION AND MANAGEMENT OF RADICULOPATHY USING 1-OXO-2-(2,6-DIOXOPIPERIDIN-3YL)-4-AMINOISOINDOLINE

1. FIELD OF THE INVENTION

This invention relates to methods of treating, preventing, modifying and managing pain, which comprise the administration of immunomodulatory compounds alone or in combination with known therapeutics. The invention also relates to pharmaceutical compositions and dosing regimens. In particular, the invention encompasses the use of immunomodulatory compounds in conjunction with neural blockade and/or other standard therapies for pain syndrome.

2. BACKGROUND OF THE INVENTION

Pain is a leading symptom of many different disorders and is defined as an unpleasant sensory and emotional experience associated with actual or potential tissue damage or described in terms of such damage. Merskey H, Bogduk N, eds., *Classification of Chronic Pain*, International Association for the Study of Pain (IASP) Task Force on Taxonomy, IASP Press: Seattle, 209-214, 1994. Because the perception of pain is highly subjective, it is one of the most difficult pathologies to diagnose and treat effectively. Pain leads to severe impairment of functional ability, which compromises the working, social, and family lives of sufferers. Around five percent of the adult population is estimated to suffer from pain sufficiently severe to cause significant disability. Chojnowska E, Stannard C. *Epidemiology of Chronic Pain*, Chapter 2, pp 15-26: T. S. Jensen, P. R. Wilson, A. S. C. Rice eds., *Clinical Pain Management Chronic Pain*, Arnold, London, 2003.

In most pain conditions, there is an increased neural input from the periphery. Sensory nerve impulses travel via the axons of primary afferent neurons to the dorsal horn of the spinal cord, where they propagate nerve impulses to dorsal horn neurons by releasing excitatory amino acids and neuropeptides at synapses. Dorsal horn projection neurons process and transfer the information about a peripheral stimuli to the brain via ascending spinal pathways. Mannion, R. J. and Woolf, C. J., *Clin. J. of Pain* 16:S144-S156 (2000).

The firing of dorsal horn projection neurons is determined not only by the excitatory input they receive, but also by inhibitory input from the spinal cord and higher nerve centers. Several brain regions contribute to descending inhibitory pathways. Nerve fibers from these pathways release inhibitory substances such as endogenous opioids, γ-aminobutyric acid ("GABA"), and serotonin at synapses with other neurons in the dorsal horn, or primary afferent neurons and inhibit nociceptive transmission. Peripheral nerve injury can produce changes in dorsal horn excitability by down-regulating the amount of inhibitory control over dorsal horn neurons through various mechanisms.

Repeated or prolonged stimulation of dorsal horn neurons due to C-nociceptor activation or damaged nerves can cause a prolonged increase in dorsal horn neuron excitability and responsiveness that can last hours longer than the stimulus. Sensitization of the dorsal horn neurons increases their excitability such that they respond to normal input in an exaggerated and extended way. It is known that such sustained activity in primary afferent C-fibers leads to both morphological and biochemical changes in the dorsal horn which may be difficult to reverse. In the dorsal horn, several changes have been noted to occur with central sensitization, including: (i) an expansion of the dorsal horn receptive field size so that a spinal neuron will respond to noxious stimuli outside the region normally served by that neuron; (ii) an increase in the magnitude and duration of the response to a given noxious stimulus (hyperalgesia); (iii) a painful response to a normally innocuous stimulus, for example, from a mechanoreceptive primary afferent Aβ-fiber (allodynia); and (iv) the spread of pain to uninjured tissue (referred pain). Koltzenburg, M. *Clin. J of Pain* 16:S131-S138 (2000); and Mannion, R. J. and Woolf, C. J., *Clin. J. of Pain* 16:S144-S156 (2000).

Central sensitization may explain, in part, the continuing pain and hyperalgesia that occurs following an injury, and may serve an adaptive purpose by encouraging protection of the injury during the healing phase. Central sensitization, however, can persist long after the injury has healed thereby supporting chronic pain. Sensitization also plays a key role in chronic pain, helping to explain why it often exceeds the provoking stimulus, both spatially and temporally, and may help explain why established pain is more difficult to suppress than acute pain. Koltzenburg, M. *Clin. J. of Pain* 16:S131-S138 (2000).

2.1 Types of Pain
  2.1.1 Nociceptive Pain
  Nociceptive pain is elicited when noxious stimuli such as inflammatory chemical mediators are released following tissue injury, disease, or inflammation and are detected by normally functioning sensory receptors (nociceptors) at the site of injury. Koltzenburg, M. *Clin. J. of Pain* 16:S131-S138 (2000). Clinical examples of nociceptive pain include but are not limited to pain associated with chemical or thermal burns, cuts and contusions of the skin, osteoarthritis, rheumatoid arthritis, tendonitis, and myofascial pain.

Nociceptors (sensory receptors) are distributed throughout the periphery of tissue. They are sensitive to noxious stimuli (e.g., thermal, mechanical, or chemical) which would damage tissue if prolonged. Activation of peripheral nociceptors by such stimuli excites discharges in two distinct types of primary afferent neurons: slowly conducting unmyelinated c-fibers and more rapidly conducting, thinly myelinated Aδ fibers. C-fibers are associated with burning pain and Aδ fibers with stabbing pain. Koltzenburg, M. *Clin. J. of Pain* 16:S131-S138 (2000); Besson, J. M. *Lancet* 353:1610-15 (1999); and Johnson, B. W. *Pain Mechanisms: Anatomy, Physiology and Neurochemistry*, Chapter 11 in *Practical Management of Pain* ed. P. Prithvi Raj. (3$^{rd}$ Ed., Mosby, Inc. St Louis, 2000). Most nociceptive pain involves signaling from both Aδ and c-types of primary afferent nerve fibers.

Peripheral nociceptors are sensitized by inflammatory mediators such as prostaglandin, substance P, bradykinin, histamine, and serotonin, as well as by intense, repeated, or prolonged noxious stimulation. In addition, cytokines and growth factors (e.g., nerve growth factor) can influence neuronal phenotype and function. Besson, J. M. *Lancet* 353: 1610-15 (1999). When sensitized, nociceptors exhibit a lower activation threshold and an increased rate of firing, which means that they generate nerve impulses more readily and more frequently. Peripheral sensitization of nociceptors plays an important role in spinal cord dorsal horn central sensitization and clinical pain states such as hyperalgesia and allodynia.

Inflammation also appears to have another important effect on peripheral nociceptors. Some C-nociceptors do not normally respond to any level of mechanical or thermal stimuli, and are only activated in the presence of inflammation or in response to tissue injury. Such nociceptors are called "silent" nociceptors, and have been identified in visceral and cutaneous tissue. Besson, J. M. *Lancet* 353:1610-15 (1999); Koltzenburg, M. *Clin. J. of Pain* 16:S131-S138 (2000).

Differences in how noxious stimuli are processed across different tissues contribute to the varying characteristics of nociceptive pain. For example, cutaneous pain is often described as a well-localized sharp, prickling, or burning sensation whereas deep somatic pain may be described as diffuse, dull, or an aching sensation. In general, there is a variable association between pain perception and stimulus intensity, as the central nervous system and general experience influence the perception of pain.

2.1.2 Neuropathic Pain

Neuropathic pain reflects injury or impairment of the nervous system, and has been defined by the IASP as "pain initiated or caused by a primary lesion or dysfunction in the nervous system." Merskey H, Bogduk N, eds., *Classification of Chronic Pain*, International Association for the Study of Pain (IASP) Task Force on Taxonomy, IASP Press: Seattle, 209-214, 1994. Some neuropathic pain is caused by injury or dysfunction of the peripheral nervous system. As a result of injury, changes in the expression of key transducer molecules, transmitters, and ion channels occur, leading to altered excitability of peripheral neurons. Johnson, B. W. *Pain Mechanisms: Anatomy, Physiology and Neurochemistry*, Chapter 11 in *Practical Management of Pain* ed. P. Prithvi Raj. ($3^{rd}$ Ed., Mosby, Inc. St Louis, 2000). Clinical examples of neuropathic pain include but are not limited to pain associated with diabetic neuropathy, postherpetic neuralgia, trigeminal neuralgia, and post-stroke pain.

Neuropathic pain is commonly associated with several distinct characteristics, such as pain which may be continuous or episodic and is described in many ways, such as burning, tingling, prickling, shooting, electric-shock-like, jabbing, squeezing, deep aching, or spasmodic. Paradoxically partial or complete sensory deficit is often present in patients with neuropathic pain who experience diminished perception of thermal and mechanical stimuli. Abnormal or unfamiliar unpleasant sensations (dysaesthesias) may also be present and contribute to patient suffering. Other features are the ability of otherwise non-noxious stimuli to produce pain (allodynia) or the disproportionate perception of pain in response to supra-threshold stimuli (hyperalgesia). Johnson, B. W. *Pain Mechanisms: Anatomy, Physiology and Neurochemistry*, Chapter 11 in *Practical Management of Pain* ed. P. Prithvi Raj. ($3^{rd}$ Ed., Mosby, Inc. St Louis, 2000); and Attal, N. *Clin. J of Pain* 16:S118-S130 (2000).

Complex regional pain syndrome (CRPS) is a type of neuropathic pain which usually affects the extremities in the absence (CRPS type I) or presence (CRPS type II) of a nerve injury. CRPS type I encompasses the condition known as reflex sympathetic dystrophy (RSD), CRPS type II encompasses the condition known as causalgia and both types have subsets consistent with sympathetic maintained pain syndrome. In 1993, a special consensus conference of the IASP addressed diagnosis and terminology of the disease, and endorsed the term CRPS with the two subtypes. Subsequent studies and conferences have refined the definitions such that the current guidelines give high sensitivity (0.70) with very high specificity (0.95). Bruehl, et al. *Pain* 81:147-154 (1999). However, there is still no general agreement on what causes the disease, or how best to treat it. Paice, E., *British Medical Journal* 310: 1645-1648 (1995).

CRPS is a multi-symptom and multi-system syndrome affecting multiple neural, bone and soft tissues, including one or more extremities, which is characterized by an intense pain. Although it was first described 130 years ago, CRPS remains poorly understood. For example, changes in peripheral and central somatosensory, autonomic, and motor processing, and a pathologic interaction of sympathetic and afferent systems have been proposed as underlying mechanisms. Wasner et al. demonstrated a complete functional loss of cutaneous sympathetic vasoconstrictor activity in an early stage of CRPS with recovery. Wasner G., Heckmann K., Maier C., *Arch Neurol* 56(5): 613-20 (1999). Kurvers et al. suggested a spinal component to microcirculatory abnormalities at stage I of CRPS, which appeared to manifest itself through a neurogenic inflammatory mechanism. Kurvers H. A., Jacobs M. J., Beuk R. J., *Pain* 60(3): 333-40 (1995). The cause of vascular abnormalities is unknown, and debate still surrounds the question of whether the sympathetic nervous system (SNS) is involved in the generation of these changes.

The actual incidence of CRPS in the U.S. is unknown, and limited information is available about the epidemiology of the disease. Both sexes are affected, but the incidence of the syndrome is higher in women. The syndrome may occur in any age group, including the pediatric population. Schwartzman R. J., *Curr Opin Neurol Neurosurg* 6(4): 531-6 (1993). Various causes that have led to CRPS include but are not limited to head injury, stroke, polio, tumor, trauma, amylotrophic lateral sclerosis (ALS), myocardial infarction, polymyalgia rheumatica, operative procedure, brachial plexopathy, cast/splint immobilization, minor extremity injury and malignancy.

Symptoms of CRPS include but are not limited to pain, autonomic dysfunction, edema, movement disorder, dystrophy, and atrophy. Schwartzman R. J., *N Engl J Med* 343(9): 654-6 (2000). The pain is described as extremely severe and unrelenting, often with a burning character. Ninety percent of all CRPS patients complain of spontaneous burning pain and allodynia, which refers to pain with light touch. Much of the difficulty clinicians have with this syndrome is the fact that pain may be far worse than what would be expected based on physical findings. Id. Pain is also accompanied by swelling and joint tenderness, increased sweating, sensitivity to temperature and light touch, as well as color change to the skin. In fact, the diagnosis of CRPS cannot be made on reports of pain alone. Patients must have signs and symptoms of sensory abnormalities as well as vascular dysfunction accompanied by excessive sweating, edema or trophic changes to the skin.

As mentioned above, the IASP has divided CRPS into two types, namely, CRPS type I (also referred to as RSD) and CRPS type II (also referred to as causalgia). These two types are differentiated mainly based upon whether the inciting incident included a definable nerve injury. CRPS type I occurs after an initial noxious event other than a nerve injury. CRPS type II occurs after nerve injury. CRPS is further divided into three distinct stages in its development and manifestation. However, the course of the disease seems to be so unpredictable between various patients that staging is not always clear or helpful in treatment. Schwartzman R. J., *N Engl J Med* 343(9): 654 (2000).

In stage I, or "early RSD," pain is more severe than would be expected from the injury, and it has a burning or aching quality. It may be increased by dependency of the limb, physical contact, or emotional upset. The affected area typically becomes edematous, may be hyperthermic or hypothermic, and may show increased nail and hair growth. Radiographs may show early bony changes. Id.

In stage II, or "established RSD," edematous tissue becomes indurated. Skin typically becomes cool and hyperhidrotic with livedo reticularis or cyanosis. Hair may be lost, and nails become ridged, cracked, and brittle. Hand dryness becomes prominent, and atrophy of skin and subcutaneous tissues becomes noticeable. Pain remains the dominant feature. It is usually constant and is increased by any stimulus to the affected area. Stiffness develops at this stage. Radiographs may show diffuse osteoporosis. Id.

In stage III, or "late RSD," pain spreads proximally. Although it may diminish in intensity, pain remains a prominent feature. Flare-ups may occur spontaneously. Irreversible tissue damage occurs, and the skin is typically thin and shiny. Edema is absent, but contractures may occur. X-ray films typically indicate marked bone demineralization. Id.

In all stages of CRPS, patients endure severe chronic pain and most patients are sleep deprived. CRPS has significant morbidity and thus raising awareness of the disease is important. Early and effective treatment may lessen the effect of CRPS in some individuals. William D. Dzwierzynski et al., *Hand Clinics* Vol 10 (1): 29-44 (1994).

2.1.3 Other Types of Pain

Visceral pain has been conventionally viewed as a variant of somatic pain, but may differ in neurological mechanisms. Visceral pain is also thought to involve silent nociceptors, visceral afferent fibers that only become activated in the presence of inflammation. Cervero, F. and Laird J. M. A., *Lancet* 353:2145-48 (1999).

Certain clinical characteristics are peculiar to visceral pain: (i) it is not evoked from all viscera and not always linked to visceral injury; (ii) it is often diffuse and poorly localized, due to the organization of visceral nociceptive pathways in the central nervous system (CNS), particularly the absence of a separate visceral sensory pathway and the low proportion of visceral afferent nerve fibers; (iii) it is sometimes referred to other non-visceral structures; and (iv) it is associated with motor and autonomic reflexes, such as nausea. Johnson, B. W., *Pain Mechanisms: Anatomy, Physiology and Neurochemistry*, Chapter 11 in *Practical Management of Pain* ed. P. Prithvi Raj. ($3^{rd}$ Ed., Mosby, Inc. St Louis, 2000); and Cervero, F. and Laird J. M. A., *Lancet* 353:2145-48 (1999).

Headaches can be classified as primary and secondary headache disorders. The pathophysiology of the two most common primary disorders, i.e., migraine and tension-type headache, is complex and not fully understood. Recent studies indicate that nociceptive input to the CNS may be increased due to the activation and sensitization of peripheral nociceptors, and the barrage of nociceptive impulses results in the activation and sensitization of second- and third-order neurons in the CNS. Thus, it is likely that central sensitization plays a role in the initiation and maintenance of migraine and tension-type headache. Johnson, B. W. *Pain Mechanisms: Anatomy, Physiology and Neurochemistry*, Chapter 11 in *Practical Management of Pain* ed. P. Prithvi Raj. ($3^{rd}$ Ed., Mosby, Inc. St Louis, 2000).

Post-operative pain, such as that resulting from trauma to tissue caused during surgery, produces a barrage of nociceptive input. Following surgery, there is an inflammatory response at the site of injury involving cytokines, neuropeptides and other inflammatory mediators. These chemicals are responsible for the sensitization and increased responsiveness to external stimuli, resulting in, for example, lowering of the threshold and an increased response to supra-threshold stimuli. Together, these processes result in peripheral and central sensitization. Johnson, B. W. *Pain Mechanisms: Anatomy, Physiology and Neurochemistry*, Chapter 11 in *Practical Management of Pain* ed. P. Prithvi Raj. ($3^{rd}$ Ed., Mosby, Inc. St Louis, 2000).

Mixed pain is chronic pain that has nociceptive and neuropathic components. For example, a particular pain can be initiated through one pain pathway and sustained through a different pain pathway. Examples of mixed pain states include, but are not limited to, cancer pain and low back pain.

2.2 Pain Treatments

Current treatment for CRPS related pain includes pain management and extensive physical therapy, which can help to prevent edema and joint contractures and can also help to minimize pain. Often, medication and neural blockade are used to help with the severe pain. Regional neural blockade is performed using Bier blocks with a variety of agents, including local anesthetics, bretylium, steroids, calcitonin, reserpine, and guanethidine. Perez R. S., et al., *J Pain Symptom Manage* 2001 June; 21(6): 511-26. Specific, selective sympathetic ganglia neural blockade is performed for both diagnostic and therapeutic purposes. The rationale for selective neural blockade is to interrupt the sympathetic nervous system and reduce the activation of the sensory nerves. Patients who fail well controlled neural blockade treatment may have sympathetic-independent CRPS. Once refractory to neural blockade, pain is typically lifelong and may be severe enough to be debilitating. Id.

Medications presently used during the treatment of chronic pain in general include non-narcotic analgesics, opioid analgesics, calcium channel blockers, muscle relaxants, and systemic corticosteroids. However, patients rarely obtain complete pain relief. Moreover, because the mechanisms of pain and autonomic dysfunction are poorly understood, the treatments are completely empirical. Between five and ten percent of patients with CRPS develop a chronic form of pain, often with severe disability and extensive use of pain medications. Therefore, there remains a need for safe and effective methods of treating and managing pain.

2.3 Immunomodulatory Compounds

A group of compounds selected for their capacity to potently inhibit TNF-α production by LPS stimulated PBMC has been investigated. L. G. Corral, et al., Ann. Rheum. Dis. 58:(Suppl I) 1107-1113 (1999). These compounds, which are referred to as IMiDs™ (Celgene Corporation) or Immunomodulatory Drugs, show not only potent inhibition of TNF-α but also marked inhibition of LPS induced monocyte IL1β and IL12 production. LPS induced IL6 is also inhibited by immunomodulatory compounds, albeit partially. These compounds are potent stimulators of LPS induced IL10. Id.

3. SUMMARY OF THE INVENTION

This invention encompasses methods of treating, preventing, modifying or managing (e.g., lengthening the time of remission) pain, which comprise administering to a patient in need thereof a therapeutically or prophylactically effective amount of an immunomodulatory compound, or a pharmaceutically acceptable salt, solvate, hydrate, stereoisomer, clathrate, or prodrug thereof.

Another embodiment of the invention encompasses the use of one or more immunomodulatory compounds in combination with other therapeutics presently used to treat or prevent pain such as, but not limited to, antidepressants, antihypertensives, anxiolytics, calcium channel blockers, muscle relaxants, non-narcotic analgesics, opioid analgesics, alpha-adrenergic receptor agonists or antagonists, anti-inflammatory agents, cox-2 inhibitors, immunomodulatory agents, immunosuppressive agents, hyperbaric oxygen, JNK inhibitors and corticosteroids.

Yet another embodiment of the invention encompasses the use of one or more immunomodulatory compounds in combination with conventional therapies used to treat, prevent or manage pain including, but not limited to, surgery, interventional procedures (e.g., neural blockade), physical therapy, and psychological therapy.

The invention further encompasses pharmaceutical compositions, single unit dosage forms, and kits suitable for use in treating, preventing, modifying and/or managing pain, which comprise an immunomodulatory compound, or a pharmaceutically acceptable salt, solvate, hydrate; stereoisomer, clathrate, or prodrug thereof.

4. DETAILED DESCRIPTION OF THE INVENTION

This invention is based, in part, on the belief that compounds disclosed herein can work alone or in combination with other drugs to effectively treat, prevent, modify and/or manage varying types and severities of pain. Without being limited by theory, compounds of the invention can, but do not necessarily, act as analgesics. In particular, because certain compounds can dramatically affect the production of cytokines (e.g., TNF-$\alpha$, IL1$\beta$, IL12 and IL-4), it is believed that they can function as "antihyperalgesics" and/or "neuromodulators" by restoring the baseline or normal pain threshold of the injured animal of human to which they are administered. Thus, compounds of the invention can act differently than analgesics, which typically diminish the response induced by stimulus, by instead altering the patient's ability to withstand that response either by suppressing the suffering associated with the pain or directly reducing the responsiveness of the nociceptors. For this reason, it is believed that compounds disclosed herein can be used to treat, prevent, modify and manage not only norciceptive pain, but other types of pain (e.g., neuropathic pain) with substantially different etiologies. Moreover, because of the unique mechanism by which certain compounds of the invention are believed to act, it is believed that they can relieve or reduce pain without incurring adverse effects (e.g., narcotic effects) typical of some analgesics (e.g., opioids), even when administered systemically.

A first embodiment of the invention encompasses methods of treating, preventing, modifying or managing pain, which comprise administering to a patient in need thereof a therapeutically or prophylactically effective amount of an immunomodulatory compound, or a pharmaceutically acceptable salt, solvate, hydrate, stereoisomer, clathrate, or prodrug thereof. The invention further relates to the treatment, prevention, modification, or management of specific types of pain including, but not limited to, nociceptive pain, neuropathic pain, mixed pain of nociceptive and neuropathic pain, visceral pain, migraine, headache and post-operative pain.

Unless otherwise indicated, the term "nociceptive pain" includes, but is not limited to, pain associated with chemical or thermal burns, cuts of the skin, contusions of the skin, osteoarthritis, rheumatoid arthritis, tendonitis, and myofascial pain.

Unless otherwise indicated, the term "neuropathic pain" includes, but is not limited to, CRPS type I, CRPS type II, reflex sympathetic dystrophy (RSD), reflex neurovascular dystrophy, reflex dystrophy, sympathetically maintained pain syndrome, causalgia, Sudeck atrophy of bone, algoneurodystrophy, shoulder hand syndrome, post-traumatic dystrophy, trigeminal neuralgia, post herpetic neuralgia, cancer related pain, phantom limb pain, fibromyalgia, chronic fatigue syndrome, spinal cord injury pain, central post-stroke pain, radiculopathy, diabetic neuropathy, post-stroke pain, luetic neuropathy, and other painful neuropathic conditions such as those induced by drugs such as vincristine, velcade and thalidomide.

As used herein, the terms "complex regional pain syndrome," "CRPS" and "CRPS and related syndromes" mean a chronic pain disorder characterized by one or more of the following: pain, whether spontaneous or evoked, including allodynia (painful response to a stimulus that is not usually painful) and hyperalgesia (exaggerated response to a stimulus that is usually only mildly painful); pain that is disproportionate to the inciting event (e.g., years of severe pain after an ankle sprain); regional pain that is not limited to a single peripheral nerve distribution; and autonomic dysregulation (e.g., edema, alteration in blood flow and hyperhidrosis) associated with trophic skin changes (hair and nail growth abnormalities and cutaneous ulceration).

Another embodiment of the invention encompasses methods of modifying or modulating the threshold, development and/or duration of pain which comprise administering to a patient in need of such modification or modulation a therapeutically or prophylactically effective amount of an immunomodulatory compound, or a pharmaceutically acceptable salt, solvate, hydrate, stereoisomer, clathrate, or prodrug thereof.

Another embodiment of the invention encompasses a pharmaceutical composition comprising an immunomodulatory compound, or a pharmaceutically acceptable salt, solvate, hydrate, stereoisomer, clathrate, or prodrug thereof, and an optional carrier.

Also encompassed by the invention are single unit dosage forms comprising an immunomodulatory compound, or a pharmaceutically acceptable salt, solvate, hydrate, stereoisomer, clathrate, or prodrug thereof, and an optional carrier.

Another embodiment of the invention encompasses a kit comprising a pharmaceutical composition comprising an immunomodulatory compound, or a pharmaceutically acceptable salt, solvate, hydrate, stereoisomer, clathrate, or prodrug thereof. The invention further encompasses kits comprising single unit dosage forms. Kits encompassed by this invention can further comprise additional active agents or combinations thereof.

Without being limited by theory, it is believed that certain immunomodulatory compounds and other medications that may be used to treat symptoms of pain can act in complementary or synergistic ways in the treatment, modification or management of pain. Therefore, one embodiment of the invention encompasses a method of treating, preventing, modifying and/or managing pain, which comprises administering to a patient in need thereof a therapeutically or prophylactically effective amount of an immunomodulatory compound, or a pharmaceutically acceptable salt, solvate, hydrate, stereoisomer, clathrate, or prodrug thereof, and a therapeutically or prophylactically effective amount of a second active agent.

Examples of second active agents include, but are not limited to, conventional therapeutics used to treat or prevent pain such as antidepressants, anticonvulsants, antihypertensives, anxiolytics, calcium channel blockers, muscle relaxants, non-narcotic analgesics, opioid analgesics, anti-inflammatories, cox-2 inhibitors, immunomodulatory agents, alpha-adrenergic receptor agonists or antagonists, immunosuppressive agents, corticosteroids, hyperbaric oxygen, ketamine, other anesthetic agents, NMDA antagonists, and other therapeutics found, for example, in the *Physician's Desk Reference* 2003.

The invention also encompasses pharmaceutical compositions, single unit dosage forms, and kits which comprise one or more immunomodulatory compounds, or a pharmaceutically acceptable salt, solvate, hydrate, stereoisomer, clathrate, or prodrug thereof, and a second active agent. For example, a kit may contain one or more compounds of the invention and an antidepressant, calcium channel blocker, non-narcotic analgesic, opioid analgesic, anti-inflammatory agent, cox-2 inhibitor, alpha-adrenergic receptor agonist or antagonist, immunomodulatory agent, immunosuppressive agent, anticonvulsant, or other drug capable of relieving or alleviating a symptom of pain.

It is further believed that particular immunomodulatory compounds may reduce or eliminate adverse effects associated with the administration of therapeutic agents used to treat pain, thereby allowing the administration of larger amounts of the agents to patients and/or increasing patient compliance. Consequently, another embodiment of the invention encompasses a method of reversing, reducing or avoiding an adverse effect associated with the administration of a second active agent in a patient suffering from pain, which comprises administering to a patient in need thereof a therapeutically or prophylactically effective amount of an immunomodulatory compound, or a pharmaceutically acceptable salt, solvate, hydrate, stereoisomer, clathrate, or prodrug thereof. Examples of adverse effects include, but are not limited to, nausea, epigastric distress, vomiting, prolonged bleeding time, respiratory depression, metabolic acidosis, hyperthermia, uriticaria, bronchoconstriction, angioneurotic edema, and Reye's syndrome.

As discussed elsewhere herein, symptoms of pain may be treated with physical therapy, psychological therapy and certain types of surgery, such as, but not limited to, selective somatic or sympathetic ganglia neural blockade. Without being limited by theory, it is believed that the combined use of such conventional therapies and an immunomodulatory compound may provide a unique and unexpected synergy to reduce complications associated with conventional therapies. Therefore, this invention encompasses a method of treating, preventing, modifying and/or managing pain, which comprises administering to a patient (e.g., a human) an immunomodulatory compound, or a pharmaceutically acceptable salt, solvate, hydrate, stereoisomer, clathrate, or prodrug thereof, before, during, or after surgery (e.g., neural blockade), physical therapy, psychological therapy or other conventional, non-drug based therapies.

4.1 Immunomodulatory Compounds

Compounds of the invention can either be commercially purchased or prepared according to the methods described in the patents or patent publications disclosed herein. Further, optically pure compositions can be asymmetrically synthesized or resolved using known resolving agents or chiral columns as well as other standard synthetic organic chemistry techniques. Compounds used in the invention may include immunomodulatory compounds that are racemic, stereomerically enriched or stereomerically pure, and pharmaceutically acceptable salts, solvates, stereoisomers, clathrates, and prodrugs thereof.

As used herein, unless otherwise indicated, the term "solvates" includes hydrates of the compounds of the invention.

Preferred compounds used in the invention are small organic molecules having a molecular weight less than about 1,000 g/mol, and are not proteins, peptides, oligonucleotides, oligosaccharides or other macromolecules.

As used herein and unless otherwise indicated, the terms "immunomodulatory compounds" and "IMiDs™" (Celgene Corporation) encompasses small organic molecules that markedly inhibit TNF-α, LPS induced monocyte IL1β and IL12, and partially inhibit IL6 production. Specific immunomodulatory compounds are discussed below.

TNF-α is an inflammatory cytokine produced by macrophages and monocytes during acute inflammation. TNF-α is responsible for a diverse range of signaling events within cells. TNF-α may play a pathological role in cancer. Without being limited by theory, one of the biological effects exerted by the immunomodulatory compounds of the invention is the reduction of synthesis of TNF-α. Immunomodulatory compounds of the invention enhance the degradation of TNF-α mRNA.

Further, without being limited by theory, immunomodulatory compounds used in the invention may also be potent co-stimulators of T cells and increase cell proliferation dramatically in a dose dependent manner. Immunomodulatory compounds of the invention may also have a greater co-stimulatory effect on the CD8+ T cell subset than on the CD4+ T cell subset. In addition, the compounds preferably have anti-inflammatory properties, and efficiently co-stimulate T cells.

Specific examples of immunomodulatory compounds, include, but are not limited to, cyano and carboxy derivatives of substituted styrenes such as those disclosed in U.S. Pat. No. 5,929,117; 1-oxo-2-(2,6-dioxo-3-fluoropiperidin-3-yl) isoindolines and 1,3-dioxo-2-(2,6-dioxo-3-fluoropiperidine-3-yl) isoindolines such as those described in U.S. Pat. Nos. 5,874,448 and 5,955,476; the tetra substituted 2-(2,6-dioxopiperidin-3-yl)-1-oxoisoindolines described in U.S. Pat. No. 5,798,368; 1-oxo and 1,3-dioxo-2-(2,6-dioxopiperidin-3-yl) isoindolines (e.g., 4-methyl derivatives of thalidomide), including, but not limited to, those disclosed in U.S. Pat. Nos. 5,635,517, 6,476,052, 6,555,554, and 6,403,613; 1-oxo and 1,3-dioxoisoindolines substituted in the 4- or 5-position of the indoline ring (e.g., 4-(4-amino-1,3-dioxoisoindoline-2-yl)-4-carbamoylbutanoic acid) described in U.S. Pat. No. 6,380,239; isoindoline-1-one and isoindoline-1,3-dione substituted in the 2-position with 2,6-dioxo-3-hydroxypiperidin-5-yl (e.g., 2-(2,6-dioxo-3-hydroxy-5-fluoropiperidin-5-yl)-4-aminoisoindolin-1-one) described in U.S. Pat. No. 6,458,810; a class of non-polypeptide cyclic amides disclosed in U.S. Pat. Nos. 5,698,579 and 5,877,200; aminothalidomide, as well as analogs, hydrolysis products, metabolites, derivatives and precursors of aminothalidomide, and substituted 2-(2,6-dioxopiperidin-3-yl) phthalimides and substituted 2-(2,6-dioxopiperidin-3-yl)-1-oxoisoindoles such as those described in U.S. Pat. Nos. 6,281,230 and 6,316,471; and isoindole-imide compounds such as those described in U.S. patent application Ser. No. 09/972,487 filed on Oct. 5, 2001, U.S. patent application Ser. No. 10/032,286 filed on Dec. 21, 2001, and International Application No. PCT/US01/50401 (International Publication No. WO 02/059106). The entireties of each of the patents and patent applications identified herein are incorporated herein by reference. Immunomodulatory compounds do not include thalidomide.

Other specific immunomodulatory compounds of the invention include, but are not limited to, 1-oxo- and 1,3 dioxo-2-(2,6-dioxopiperidin-3-yl) isoindolines substituted with amino in the benzo ring as described in U.S. Pat. No. 5,635,517 which is incorporated herein by reference. These compounds have the structure I:

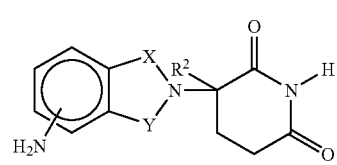

in which one of X and Y is C—O, the other of X and Y is C═O or CH$_2$, and R$^2$ is hydrogen or lower alkyl, in particular methyl. Specific immunomodulatory compounds include, but are not limited to:

1-oxo-2-(2,6-dioxopiperidin-3-yl)-4-aminoisoindoline;
1-oxo-2-(2,6-dioxopiperidin-3-yl)-5-aminoisoindoline;
1-oxo-2-(2,6-dioxopiperidin-3-yl)-6-aminoisoindoline;
1-oxo-2-(2,6-dioxopiperidin-3-yl)-7-aminoisoindoline;
1,3-dioxo-2-(2,6-dioxopiperidin-3-yl)-4-aminoisoindoline; and
1,3-dioxo-2-(2,6-dioxopiperidin-3-yl)-5-aminoisoindoline.

Other specific immunomodulatory compounds of the invention belong to a class of substituted 2-(2,6-dioxopiperidin-3-yl) phthalimides and substituted 2-(2,6-dioxopiperidin-3-yl)-1-oxoisoindoles, such as those described in U.S. Pat. Nos. 6,281,230; 6,316,471; 6,335,349; and 6,476,052, and International Patent Application No. PCT/US97/13375 (International Publication No. WO 98/03502), each of which is incorporated herein by reference. Representative compounds are of formula:

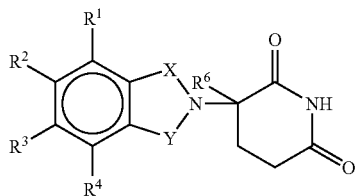

in which:

one of X and Y is C═O and the other of X and Y is C═O or CH$_2$;

(i) each of R$^1$, R$^2$, R$^3$, and R$^4$, independently of the others, is halo, alkyl of 1 to 4 carbon atoms, or alkoxy of 1 to 4 carbon atoms or (ii) one of R$^1$, R$^2$, R$^3$, and R$^4$ is —NHR$^5$ and the remaining of R$^1$, R$^2$, R$^3$, and R$^4$ are hydrogen;

R$^5$ is hydrogen or alkyl of 1 to 8 carbon atoms;

R$^6$ is hydrogen, alkyl of 1 to 8 carbon atoms, benzyl, or halo;

provided that R$^6$ is other than hydrogen if X and Y are C═O and (i) each of R$^1$, R$^2$, R$^3$, and R$^4$ is fluoro or (ii) one of R$^1$, R$^2$, R$^3$, or R$^4$ is amino.

Compounds representative of this class are of the formulas:

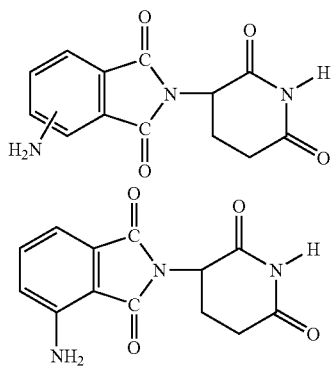

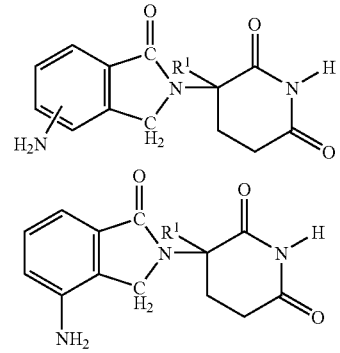

wherein R$^1$ is hydrogen or methyl. In a separate embodiment, the invention encompasses the use of enantiomerically pure forms (e.g. optically pure (R) or (S) enantiomers) of these compounds.

Still other specific immunomodulatory compounds of the invention belong to a class of isoindole-imides disclosed in U.S. Patent Application Publication Nos. US 2003/0096841 and US 2003/0045552, and International Application No. PCT/US01/50401 (International Publication No. WO 02/059106), each of which are incorporated herein by reference. Representative compounds are of formula II:

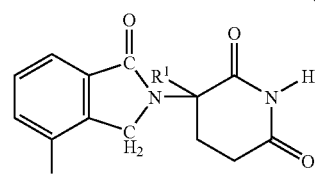

and pharmaceutically acceptable salts, hydrates, solvates, clathrates, enantiomers, diastereomers, racemates, and mixtures of stereoisomers thereof, wherein:

one of X and Y is C═O and the other is CH$_2$ or C═O;

R$^1$ is H, (C$_1$-C$_8$)alkyl, (C$_3$-C$_7$)cycloalkyl, (C$_2$-C$_8$)alkenyl, (C$_2$-C$_8$)alkynyl, benzyl, aryl, (C$_0$-C$_4$)alkyl-(C$_1$-C$_6$)heterocycloalkyl, (C$_0$-C$_4$)alkyl-(C$_2$-C$_5$)heteroaryl, C(O)R$^3$, C(S)R$^3$, C(O)OR$^4$, (C$_1$-C$_8$)alkyl-N(R$^6$)$_2$, (C$_1$-C$_8$)alkyl-OR$^5$, (C$_1$-C$_8$)alkyl-C(O)OR$^5$, C(O)NHR$^3$, C(S)NHR$^3$, C(O)NR$^3$R$^{3'}$, C(S)NR$^3$R$^{3'}$ or (C$_1$-C$_8$)alky-O(CO)R$^5$;

R$^2$ is H, F, benzyl, (C$_1$-C$_8$)alkyl, (C$_2$-C$_8$)alkenyl, or (C$_2$-C$_8$)alkynyl;

R$^3$ and R$^{3'}$ are independently (C$_1$-C$_8$)alkyl, (C$_3$-C$_7$)cycloalkyl, (C$_2$-C$_8$)alkenyl, (C$_2$-C$_8$)alkynyl, benzyl, aryl, (C$_0$-C$_4$)alkyl-(C$_1$-C$_6$)heterocycloalkyl, (C$_0$-C$_4$)alkyl-(C$_2$-C$_5$)heteroaryl, (C$_0$-C$_8$)alkyl-N(R$^6$)$_2$, (C$_1$-C$_8$)alkyl-OR$^5$, (C$_1$-C$_8$)alkyl-(O)OR$^5$, (C$_1$-C$_8$)alkyl-O(CO)R$^5$, or C(O)OR$^5$;

R$^4$ is (C$_1$-C$_8$)alkyl, (C$_2$-C$_8$)alkenyl, (C$_2$-C$_8$)alkynyl, (C$_1$-C$_4$)alkyl-OR$^5$, benzyl, aryl, (C$_0$-C$_4$)alkyl-(C$_1$-C$_6$)heterocycloalkyl, or (C$_0$-C$_4$)alkyl-(C$_2$-C$_5$)heteroaryl;

R$^5$ is (C$_1$-C$_8$)alkyl, (C$_2$-C$_8$)alkenyl, (C$_2$-C$_8$)alkynyl, benzyl, aryl, or (C$_2$-C$_5$)heteroaryl;

each occurrence of R$^6$ is independently H, (C$_1$-C$_8$)alkyl, (C$_2$-C$_8$)alkenyl, (C$_2$-C$_8$)alkynyl, benzyl, aryl, (C$_2$-C$_5$)heteroaryl, or $(C_0\text{-}C_8)$alkyl-$C(O)O\text{---}R^5$ or the $R^6$ groups can join to form a heterocycloalkyl group;

n is 0 or 1; and

* represents a chiral-carbon center.

In specific compounds of formula II, when n is 0 then $R^1$ is $(C_3\text{-}C_7)$cycloalkyl, $(C_2\text{-}C_8)$alkenyl, $(C_2\text{-}C_8)$alkynyl, benzyl, aryl, $(C_0\text{-}C_4)$alkyl-$(C_1\text{-}C_6)$heterocycloalkyl, $(C_0\text{-}C_4)$alkyl-$(C_2\text{-}C_5)$heteroaryl, $C(O)R^3$, $C(O)OR^4$, $(C_1\text{-}C_8)$alkyl-$N(R^6)_2$, $(C_1\text{-}C_8)$alkyl-$OR^5$, $(C_1\text{-}C_8)$alkyl-$C(O)OR^5$, $C(S)NHR^3$, or $(C_1\text{-}C_8)$alkyl-$O(CO)R^5$;

$R^2$ is H or $(C_1\text{-}C_8)$alkyl; and $R^3$ is $(C_1\text{-}C_8)$alkyl, $(C_3\text{-}C_7)$cycloalkyl, $(C_2\text{-}C_8)$alkenyl, $(C_2\text{-}C_8)$alkynyl, benzyl, aryl, $(C_0\text{-}C_4)$alkyl-$(C_1\text{-}C_6)$heterocycloalkyl, $(C_0\text{-}C_4)$alkyl-$(C_2\text{-}C_5)$heteroaryl, $(C_5\text{-}C_8)$alkyl-$N(R^6)_2$; $(C_0\text{-}C_8)$alky-$NH\text{---}C(O)O\text{---}R^5$; $(C_1\text{-}C_8)$alkyl-$OR^5$, $(C_1\text{-}C_8)$alkyl-$C(O)OR^5$, $(C_1\text{-}C_8)$alkyl-$O(CO)R^5$, or $C(O)OR^5$; and the other variables have the same definitions.

In other specific compounds of formula II, $R^2$ is H or $(C_1\text{-}C_4)$alkyl.

In other specific compounds of formula II, $R^1$ is $(C_1\text{-}C_8)$alkyl or benzyl.

In other specific compounds of formula II, $R^1$ is H, $(C_1\text{-}C_8)$alkyl, benzyl, $CH_2OCH_3$, $CH_2CH_2OCH_3$, or

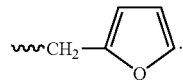

In another embodiment of the compounds of formula II, $R^1$ is

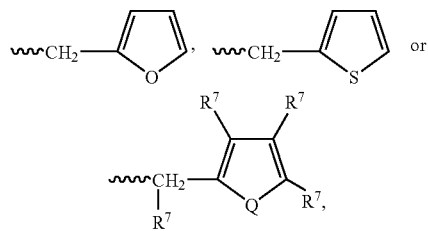

wherein Q is O or S, and each occurrence of $R^7$ is independently H, $(C_1\text{-}C_8)$alkyl, $(C_3\text{-}C_7)$cycloalkyl, $(C_2\text{-}C_8)$alkenyl, $(C_2\text{-}C_8)$alkynyl, benzyl, aryl, halogen, $(C_0\text{-}C_4)$alkyl-$(C_1\text{-}C_6)$heterocycloalkyl, $(C_0\text{-}C_4)$alkyl-$(C_2\text{-}C_5)$heteroaryl, $(C_0\text{-}C_8)$alkyl-$N(R^6)_2$, $(C_1\text{-}C_8)$alkyl-$OR^5$, $(C_1\text{-}C_8)$alkyl-$C(O)OR^5$, $(C_1\text{-}C_8)$alkyl-$O(CO)R^5$, or $C(O)OR^5$, or adjacent occurrences of $R^7$ can be taken together to form a bicyclic alkyl or aryl ring.

In other specific compounds of formula II, $R^1$ is $C(O)R^3$.

In other specific compounds of formula II, $R^3$ is $(C_0\text{-}C_4)$alkyl-$(C_2\text{-}C_5)$heteroaryl, $(C_1\text{-}C_8)$alkyl, aryl, or $(C_0\text{-}C_4)$alkyl-$OR^5$.

In other specific compounds of formula II, heteroaryl is pyridyl, furyl, or thienyl.

In other specific compounds of formula II, $R^1$ is $C(O)OR^4$.

In other specific compounds of formula II, the H of $C(O)NHC(O)$ can be replaced with $(C_1\text{-}C_4)$alkyl, aryl, or benzyl.

Further examples of the compounds in this class include, but are not limited to: [2-(2,6-dioxo-piperidin-3-yl)-1,3-dioxo-2,3-dihydro-1H-isoindol-4-ylmethyl]-amide; (2-(2,6-dioxo-piperidin-3-yl)-1,3-dioxo-2,3-dihydro-1H-isoindol-4-ylmethyl)-carbamic acid tert-butyl ester; 4-(aminomethyl)-2-(2,6-dioxo(3-piperidyl))-isoindoline-1,3-dione; N-(2-(2,6-dioxo-piperidin-3-yl)-1,3-dioxo-2,3-dihydro-1H-isoindol-4-ylmethyl)-acetamide; N-{(2-(2,6-dioxo(3-piperidyl)-1,3-dioxoisoindolin-4-yl)methyl}cyclopropyl-carboxamide; 2-chloro-N-{(2-(2,6-dioxo(3-piperidyl))-1,3-dioxoisoindolin-4-yl)methyl}acetamide; N-(2-(2,6-dioxo(3-piperidyl))-1,3-dioxoisoindolin-4-yl)-3-pyridylcarboxamide; 3-{1-oxo-4-(benzylamino)isoindolin-2-yl}piperidine-2,6-dione; 2-(2,6-dioxo(3-piperidyl))-4-(benzylamino)isoindoline-1,3-dione; N-{(2-(2,6-dioxo(3-piperidyl))-1,3-dioxoisoindolin-4-yl)methyl}propanamide; N-{(2-(2,6-dioxo(3-piperidyl))-1,3-dioxoisoindolin-4-yl)methyl}-3-pyridylcarboxamide; N-{(2-(2,6-dioxo(3-piperidyl))-1,3-dioxoisoindolin-4-yl) methyl}heptanamide; N-{(2-(2,6-dioxo(3-piperidyl))-1,3-dioxoisoindolin-4-yl)methyl}-2-furylcarboxamide; {N-(2-(2,6-dioxo(3-piperidyl))-1,3-dioxoisoindolin-4-yl) carbamoyl}methyl acetate; N-(2-(2,6-dioxo(3-piperidyl))-1,3-dioxoisoindolin-4-yl)pentanamide; N-(2-(2,6-dioxo(3-piperidyl))-1,3-dioxoisoindolin-4-yl)-2-thienylcarboxamide; N-{[2-(2,6-dioxo(3-piperidyl))-1,3-dioxoisoindolin-4-yl]methyl}(butylamino)carboxamide; N-{[2-(2,6-dioxo(3-piperidyl))-1,3-dioxoisoindolin-4-yl]methyl}(octylamino)carboxamide; and N-{[2-(2,6-dioxo(3-piperidyl))-1,3-dioxoisoindolin-4-yl]methyl}(benzylamino) carboxamide.

Still other specific immunomodulatory compounds of the invention belong to a class of isoindole-imides disclosed in U.S. Patent Application Publication Nos. US 2002/0045643, International Publication No. WO 98/54170, and U.S. Pat. No. 6,395,754, each of which is incorporated herein by reference. Representative compounds are of formula III:

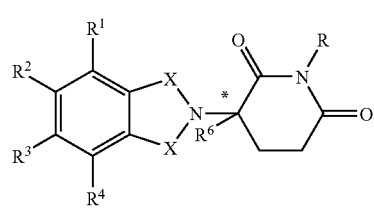

and pharmaceutically acceptable salts, hydrates, solvates, clathrates, enantiomers, diastereomers, racemates, and mixtures of stereoisomers thereof, wherein:

one of X and Y is C=O and the other is $CH_2$ or C=O;

R is H or $CH_2OCOR'$;

(i) each of $R^1$, $R^2$, $R^3$, or $R^4$, independently of the others, is halo, alkyl of 1 to 4 carbon atoms, or alkoxy of 1 to 4 carbon atoms or (ii) one of $R^1$, $R^2$, $R^3$, or $R^4$ is nitro or —$NHR^5$ and the remaining of $R^1$, $R^2$, $R^3$, or $R^4$ are hydrogen;

$R^5$ is hydrogen or alkyl of 1 to 8 carbons $R^6$ hydrogen, alkyl of 1 to 8 carbon atoms, benzo, chloro, or fluoro;

R' is $R^7$—$CHR^{10}$—$N(R^8R^9)$;

$R^7$ is m-phenylene or p-phenylene or —$(C_nH_{2n})$— in which n has a value of 0 to 4;

each of $R^8$ and $R^9$ taken independently of the other is hydrogen or alkyl of 1 to 8 carbon atoms, or $R^8$ and $R^9$ taken together are tetramethylene, pentamethylene, hexamethylene, or —$CH_2CH_2X_1CH_2CH_2$— in which $X_1$ is —O—, —S—, or —NH—;

$R^{10}$ is hydrogen, alkyl of to 8 carbon atoms, or phenyl; and

* represents a chiral-carbon center.

Other representative compounds are of formula:

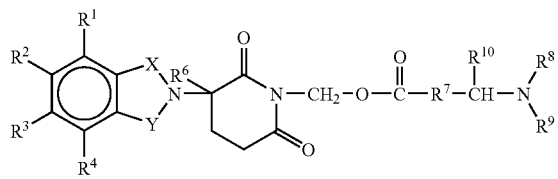

wherein:
one of X and Y is C=O and the other of X and Y is C=O or CH$_2$;
(i) each of R$^1$, R$^2$, R$^3$, or R$^4$, independently of the others, is halo, alkyl of 1 to 4 carbon atoms, or alkoxy of 1 to 4 carbon atoms or (ii) one of R$^1$, R$^2$, R$^3$, and R$^4$ is —NHR$^5$ and the remaining of R$^1$, R$^2$, R$^3$, and R$^4$ are hydrogen;
R$^5$ is hydrogen or alkyl of 1 to 8 carbon atoms;
R$^6$ is hydrogen, alkyl of 1 to 8 carbon atoms, benzo, chloro, or fluoro;
R$^7$ is m-phenylene or p-phenylene or —(C$_n$H$_{2n}$)— in which n has a value of 0 to 4;
each of R$^8$ and R$^9$ taken independently of the other is hydrogen or alkyl of 1 to 8 carbon atoms, or R$^8$ and R$^9$ taken together are tetramethylene, pentamethylene, hexamethylene, or —CH$_2$CH$_2$X$^1$CH$_2$CH$_2$— in which X$^1$ is —O—, —S—, or —NH—;
R$^{10}$ is hydrogen, alkyl of to 8 carbon atoms, or phenyl.

Other representative compounds are of formula:

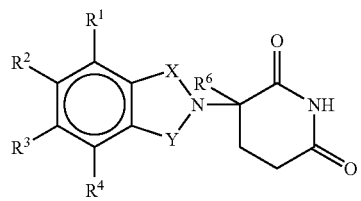

in which
one of X and Y is C=O and the other of X and Y is C=O or CH$_2$;
each of R$^1$, R$^2$, R$^3$, and R$^4$, independently of the others, is halo, alkyl of 1 to 4 carbon atoms, or alkoxy of 1 to 4 carbon atoms or (ii) one of R$^1$, R$^2$, R$^3$, and R$^4$ is nitro or protected amino and the remaining of R$^1$, R$^2$, R$^3$, and R$^4$ are hydrogen; and
R$^6$ is hydrogen, alkyl of 1 to 8 carbon atoms, benzo, chloro, or fluoro.

Other representative compounds are of formula:

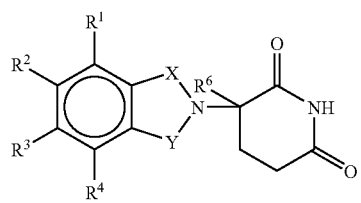

in which:
one of X and Y is C=O and the other of X and Y is C=O or CH$_2$;
(i) each of R$^1$, R$^2$, R$^3$, and R$^4$, independently of the others, is halo, alkyl of 1 to 4 carbon atoms, or alkoxy of 1 to 4 carbon atoms or (ii) one of R$^1$, R$^2$, R$^3$, and R$^4$ is —NHR$^5$ and the remaining of R$^1$, R$^2$, R$^3$, and R$^4$ are hydrogen;
R$^5$ is hydrogen, alkyl of 1 to 8 carbon atoms, or CO—R$^7$—CH(R$^{10}$)NR$^8$R$^9$ in which each of R$^7$, R$^8$, R$^9$, and R$^{10}$ is as herein defined; and
R$^6$ is alkyl of 1 to 8 carbon atoms, benzo, chloro, or fluoro.

Specific examples of the compounds are of formula:

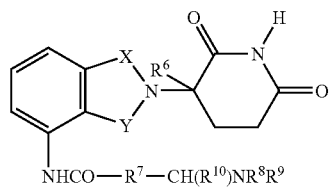

in which:
one of X and Y is C=O and the other of X and Y is C=O or CH$_2$;
R$^6$ is hydrogen, alkyl of 1 to 8 carbon atoms, benzyl, chloro, or fluoro;
R$^7$ is m-phenylene, p-phenylene or —(CH$_n$H$_{2n}$)— in which n has a value of 0 to 4;
each of R$^8$ and R$^9$ taken independently of the other is hydrogen or alkyl of 1 to 8 carbon atoms, or R$^8$ and R$^9$ taken together are tetramethylene, pentamethylene, hexamethylene, or —CH$_2$CH$_2$X$^1$CH$_2$CH$_2$— in which X$^1$ is —O—, —S— or —NH—; and
R$^{10}$ is hydrogen, alkyl of 1 to 8 carbon atoms, or phenyl.

The most preferred immunomodulatory compounds of the invention are 4-(amino)-2-(2,6-dioxo(3-piperidyl))-isoindoline-1,3-dione and 3-(4-amino-1-oxo-1,3-dihydro-isoindol-2-yl)-piperidine-2,6-dione. The compounds can be obtained via standard, synthetic methods (see e.g., U.S. Pat. No. 5,635,517, incorporated herein by reference). The compounds are available from Celgene Corporation, Warren, N.J. 4-(Amino)-2-(2,6-dioxo(3-piperidyl))-isoindoline-1,3-dione has the following chemical structure:

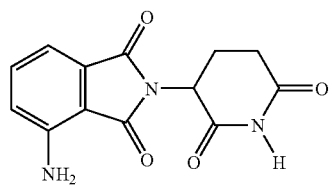

The compound 3-(4-amino-1-oxo-1,3-dihydro-isoindol-2-yl)-piperidine-2,6-dione has the following chemical structure:

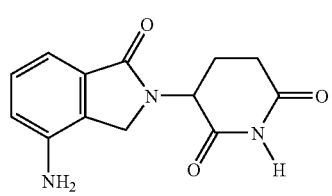

In another embodiment, specific immunomodulatory compounds of the invention encompass polymorphic forms of 3-(4-amino-1-oxo-1,3 dihydro-isoindol-2-yl)-piperidene-2,6-dione such as Form A, B, C, D, E, F, G and H, disclosed in U.S. provisional application No. 60/499,723 filed on Sep. 4, 2003, which is incorporated herein by reference. For example, Form A of 3-(4-amino-1-oxo-1,3 dihydro-isoindol-2-yl)-piperidene-2,6-dione is an unsolvated, crystalline material that can be obtained from non-aqueous solvent systems. Form A has an X-ray powder diffraction pattern comprising significant peaks at approximately 8, 14.5, 16, 17.5, 20.5, 24 and 26 degrees 2θ, and has a differential scanning calorimetry melting temperature maximum of about 270° C.

Form B of 3-(4-amino-1-oxo-1,3 dihydro-isoindol-2-yl)-piperidene-2,6-dione is a hemihydrated, crystalline material that can be obtained from various solvent systems, including, but not limited to, hexane, toluene, and water. Form B has an X-ray powder diffraction pattern comprising significant peaks at approximately 16, 18, 22 and 27 degrees 2θ, and has a differential scanning calorimetry melting temperature maximum of about 268° C.

Form C of 3-(4-amino-1-oxo-1,3 dihydro-isoindol-2-yl)-piperidene-2,6-dione is a hemisolvated crystalline material that can be obtained from solvents such as, but not limited to, acetone. Form C has an X-ray powder diffraction pattern comprising significant peaks at approximately 15.5 and 25 degrees 2θ, and has a differential scanning calorimetry melting temperature maximum of about 269° C.

Form D of 3-(4-amino-1-oxo-1,3 dihydro-isoindol-2-yl)-piperidene-2,6-dione is a crystalline, solvated polymorph prepared from a mixture of acetonitrile and water. Form D has an X-ray powder diffraction pattern comprising significant peaks at approximately 27 and 28 degrees 2θ, and has a differential scanning calorimetry melting temperature maximum of about 270° C.

Form E of 3-(4-amino-1-oxo-1,3 dihydro-isoindol-2-yl)-piperidene-2,6-dione is a dihydrated, crystalline material that can be obtained by slurrying 3-(4-amino-1-oxo-1,3 dihydro-isoindol-2-yl)-piperidene-2,6-dione in water and by a slow evaporation of 3-(4-amino-1-oxo-1,3 dihydro-isoindol-2-yl)-piperidene-2,6-dione in a solvent system with a ratio of about 9:1 acetone:water. Form E has an X-ray powder diffraction pattern comprising significant peaks at approximately 20, 24.5 and 29 degrees 2θ, and has a differential scanning calorimetry melting temperature maximum of about 269° C.

Form F of 3-(4-amino-1-oxo-1,3 dihydro-isoindol-2-yl)-piperidene-2,6-dione is an unsolvated, crystalline material that can be obtained from the dehydration of Form E. Form F has an X-ray powder diffraction pattern comprising significant peaks at approximately 19, 19.5 and 25 degrees 2θ, and has a differential scanning calorimetry melting temperature maximum of about 269° C.

Form G of 3-(4-amino-1-oxo-1,3 dihydro-isoindol-2-yl)-piperidene-2,6-dione is an unsolvated, crystalline material that can be obtained from slurrying forms B and E in a solvent such as, but not limited to, tetrahydrofuran (THF). Form G has an X-ray powder diffraction pattern comprising significant peaks at approximately 21, 23 and 24.5 degrees 2θ, and has a differential scanning calorimetry melting temperature maximum of about 267° C.

Form H of 3-(4-amino-1-oxo-1,3 dihydro-isoindol-2-yl)-piperidene-2,6-dione is a partially hydrated crystalline material that can be obtained by exposing Form E to 0% relative humidity. Form H has an X-ray powder diffraction pattern comprising significant peaks at approximately 15, 26 and 31 degrees 2θ, and has a differential scanning calorimetry melting temperature maximum of about 269° C.

Other specific immunomodulatory compounds of the invention include, but are not limited to, 1-oxo-2-(2,6-dioxo-3-fluoropiperidin-3-yl) isoindolines and 1,3-dioxo-2-(2,6-dioxo-3-fluoropiperidine-3-yl) isoindolines such as those described in U.S. Pat. Nos. 5,874,448 and 5,955,476, each of which is incorporated herein by reference. Representative compounds are of formula:

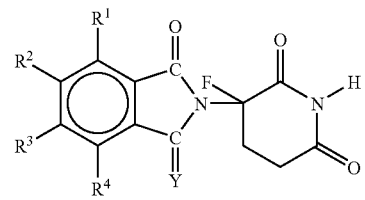

wherein Y is oxygen or $H^2$ and each of $R^1$, $R^2$, $R^3$, and $R^4$, independently of the others, is hydrogen, halo, alkyl of 1 to 4 carbon atoms, alkoxy of 1 to 4 carbon atoms, or amino.

Other specific immunomodulatory compounds of the invention include, but are not limited to, the tetra substituted 2-(2,6-dioxopiperidin-3-yl)-1-oxoisoindolines described in U.S. Pat. No. 5,798,368, which is incorporated herein by reference. Representative compounds are of formula:

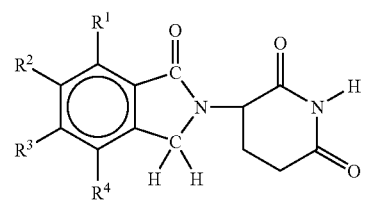

wherein each of $R^1$, $R^2$, $R^3$, and $R^4$, independently of the others, is halo, alkyl of 1 to 4 carbon atoms, or alkoxy of 1 to 4 carbon atoms.

Other specific immunomodulatory compounds of the invention include, but are not limited to, 1-oxo and 1,3-dioxo-2-(2,6-dioxopiperidin-3-yl) isoindolines disclosed in U.S. Pat. No. 6,403,613, which is incorporated herein by reference. Representative compounds are of formula:

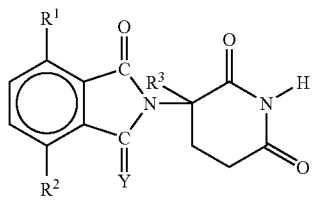

in which

Y is oxygen or $H_2$, a first of $R^1$ and $R^2$ is halo, alkyl, alkoxy, alkylamino, dialkylamino, cyano, or carbamoyl, the second of $R^1$ and $R^2$, independently of the first, is hydrogen, halo, alkyl, alkoxy, alkylamino, dialkylamino, cyano, or carbamoyl, and R³ is hydrogen, alkyl, or benzyl.

Specific examples of the compounds are of formula:

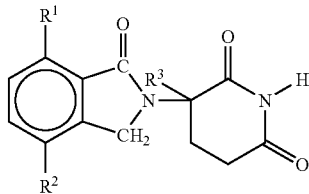

wherein a first of R¹ and R² is halo, alkyl of from 1 to 4 carbon atoms, alkoxy of from 1 to 4 carbon atoms, dialkylamino in which each alkyl is of from 1 to 4 carbon atoms, cyano, or carbamoyl, the second of R¹ and R², independently of the first, is hydrogen, halo, alkyl of from 1 to 4 carbon atoms, alkoxy of from 1 to 4 carbon atoms, alkylamino in which alkyl is of from 1 to 4 carbon atoms, dialkylamino in which each alkyl is of from 1 to 4 carbon atoms, cyano, or carbamoyl, and R³ is hydrogen, alkyl of from 1 to 4 carbon atoms, or benzyl. Other representative compounds are of formula:

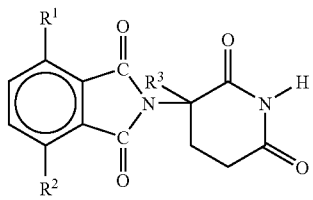

wherein a first of R¹ and R² is halo, alkyl of from 1 to 4 carbon atoms, alkoxy of from 1 to 4 carbon atoms, dialkylamino in which each alkyl is of from 1 to 4 carbon atoms, cyano, or carbamoyl, the second of R¹ and R², independently of the first, is hydrogen, halo, alkyl of from 1 to 4 carbon atoms, alkoxy of from 1 to 4 carbon atoms, alkylamino in which alkyl is of from 1 to 4 carbon atoms, dialkylamino in which each alkyl is of from 1 to 4 carbon atoms, cyano, or carbamoyl, and R³ is hydrogen, alkyl of from 1 to 4 carbon atoms, or benzyl.

Other specific immunomodulatory compounds of the invention include, but are not limited to, 1-oxo and 1,3-dioxoisoindolines substituted in the 4- or 5-position of the indoline ring described in U.S. Pat. No. 6,380,239, which is incorporated herein by reference. Representative compounds are of formula:

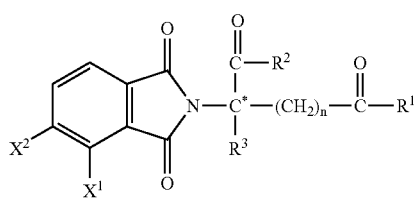

in which the carbon atom designated C* constitutes a center of chirality (when n is not zero and R¹ is not the same as R²); one of X¹ and X² is amino, nitro, alkyl of one to six carbons, or NH-Z, and the other of X¹ or X² is hydrogen; each of R¹ and R² independent of the other, is hydroxy or NH-Z; R³ is hydrogen, alkyl of one to six carbons, halo, or haloalkyl; Z is hydrogen, aryl, alkyl of one to six carbons, formyl, or acyl of one to six carbons; and n has a value of 0, 1, or 2; provided that if X¹ is amino, and n is 1 or 2, then R¹ and R² are not both hydroxy; and the salts thereof. Further representative compounds are of formula:

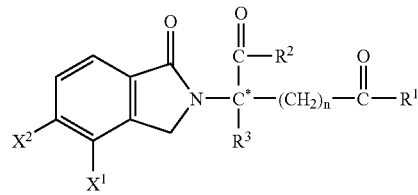

in which the carbon atom designated C* constitutes a center of chirality when n is not zero and R¹ is not R²; one of X¹ and X² is amino, nitro, alkyl of one to six carbons, or NH-Z, and the other of X¹ or X² is hydrogen; each of R¹ and R² independent of the other, is hydroxy or NH-Z; R³ is alkyl of one to six carbons, halo, or hydrogen; Z is hydrogen, aryl or an alkyl or acyl of one to six carbons; and n has a value of 0, 1, or 2.

Other representative compounds are of formula:

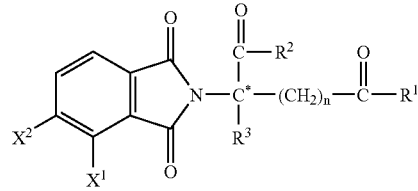

in which the carbon atom designated C* constitutes a center of chirality when n is not zero and R¹ is not R²; one of X¹ and X² is amino, nitro, alkyl of one to six carbons, or NH-Z, and the other of X¹ or X² is hydrogen; each of R¹ and R² independent of the other, is hydroxy or NH-Z; R³ is alkyl of one to six carbons, halo, or hydrogen; Z is hydrogen, aryl, or an alkyl or acyl of one to six carbons; and n has a value of 0, 1, or 2; and the salts thereof. Specific examples of the compounds are of formula:

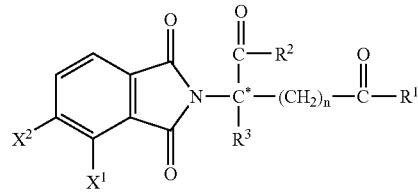

wherein one of X¹ and X² is nitro, or NH-Z, and the other of X¹ or X² is hydrogen;

each of R¹ and R², independent of the other, is hydroxy or NH-Z;

$R^3$ is alkyl of one to six carbons, halo, or hydrogen;

Z is hydrogen, phenyl, an acyl of one to six carbons, or an alkyl of one to six carbons; and n has a value of 0, 1, or 2;

provided that if one of $X^1$ and $X^2$ is nitro, and n is 1 or 2, then $R^1$ and $R^2$ are other than hydroxy; and if —$COR^1$ and —$(CH_2)_nCOR^2$ are different, the carbon atom designated C* constitutes a center of chirality. Other representative compounds are of formula:

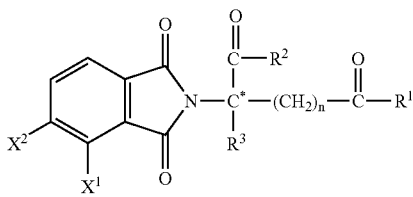

wherein one of $X^1$ and $X^2$ is alkyl of one to six carbons;

each of $R^1$ and $R^2$, independent of the other, is hydroxy or NH-Z;

$R^3$ is alkyl of one to six carbons, halo, or hydrogen;

Z is hydrogen, phenyl, an acyl of one to six carbons, or an alkyl of one to six carbons; and n has a value of 0, 1, or 2; and if —$COR^1$ and —$(CH_2)_nCOR^2$ are different, the carbon atom designated C* constitutes a center of chirality.

Still other specific immunomodulatory compounds of the invention include, but are not limited to, isoindoline-1-one and isoindoline-1,3-dione substituted in the 2-position with 2,6-dioxo-3-hydroxypiperidin-5-yl described in U.S. Pat. No. 6,458,810, which is incorporated herein by reference. Representative compounds are of formula:

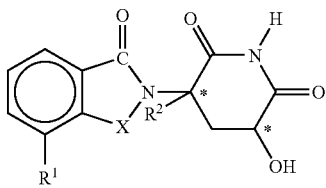

wherein:

the carbon atoms designated * constitute centers of chirality;

X is —C(O)— or —$CH_2$—;

$R^1$ is alkyl of 1 to 8 carbon atoms or —$NHR^3$;

$R^2$ is hydrogen, alkyl of 1 to 8 carbon atoms, or halogen; and $R^3$ is hydrogen, alkyl of 1 to 8 carbon atoms, unsubstituted or substituted with alkoxy of 1 to 8 carbon atoms, halo, amino, or alkylamino of 1 to 4 carbon atoms, cycloalkyl of 3 to 18 carbon atoms, phenyl, unsubstituted or substituted with alkyl of 1 to 8 carbon atoms, alkoxy of 1 to 8 carbon atoms, halo, amino, or alkylamino of 1 to 4 carbon atoms, benzyl, unsubstituted or substituted with alkyl of 1 to 8 carbon atoms, alkoxy of 1 to 8 carbon atoms, halo, amino, or alkylamino of 1 to 4 carbon atoms, or —$COR^4$ in which $R^4$ is hydrogen, alkyl of 1 to 8 carbon atoms, unsubstituted or substituted with alkoxy of 1 to 8 carbon atoms, halo, amino, or alkylamino of 1 to 4 carbon atoms, cycloalkyl of 3 to 18 carbon atoms, phenyl, unsubstituted or substituted with alkyl of 1 to 8 carbon atoms, alkoxy of 1 to 8 carbon atoms, halo, amino, or alkylamino of 1 to 4 carbon atoms, or benzyl, unsubstituted or substituted with alkyl of 1 to 8 carbon atoms, alkoxy of 1 to 8 carbon atoms, halo, amino, or alkylamino of 1 to 4 carbon atoms.

Compounds of the invention can either be commercially purchased or prepared according to the methods described in the patents or patent publications disclosed herein. Further, optically pure compounds can be asymmetrically synthesized or resolved using known resolving agents or chiral columns as well as other standard synthetic organic chemistry techniques.

As used herein and unless otherwise indicated, the term "pharmaceutically acceptable salt" encompasses non-toxic acid and base addition salts of the compound to which the term refers. Acceptable non-toxic acid addition salts include those derived from organic and inorganic acids or bases know in the art, which include, for example, hydrochloric acid, hydrobromic acid, phosphoric acid, sulfuric acid, methanesulphonic acid, acetic acid, tartaric acid, lactic acid, succinic acid, citric acid, malic acid, maleic acid, sorbic acid, aconitic acid, salicylic acid, phthalic acid, embolic acid, enanthic acid, and the like.

Compounds that are acidic in nature are capable of forming salts with various pharmaceutically acceptable bases. The bases that can be used to prepare pharmaceutically acceptable base addition salts of such acidic compounds are those that form non-toxic base addition salts, i.e., salts containing pharmacologically acceptable cations such as, but not limited to, alkali metal or alkaline earth metal salts and the calcium, magnesium, sodium or potassium salts in particular. Suitable organic bases include, but are not limited to, N,N-dibenzylethylenediamine, chloroprocaine, choline, diethanolamine, ethylenediamine, meglumaine (N-methylglucamine), lysine, and procaine.

As used herein and unless otherwise indicated, the term "prodrug" means a derivative of a compound that can hydrolyze, oxidize, or otherwise react under biological conditions (in vitro or in vivo) to provide the compound. Examples of prodrugs include, but are not limited to, derivatives of immunomodulatory compounds of the invention that comprise biohydrolyzable moieties such as biohydrolyzable amides, biohydrolyzable esters, biohydrolyzable carbamates, biohydrolyzable carbonates, biohydrolyzable ureides, and biohydrolyzable phosphate analogues. Other examples of prodrugs include derivatives of immunomodulatory compounds of the invention that comprise —NO, —$NO_2$, —ONO, or —$ONO_2$ moieties. Prodrugs can typically be prepared using well-known methods, such as those described in 1 *Burger's Medicinal Chemistry and Drug Discovery*, 172-178, 949-982 (Manfred E. Wolff ed., 5th ed. 1995), and *Design of Prodrugs* (H. Bundgaard ed., Elselvier, New York 1985).

As used herein and unless otherwise indicated, the terms "biohydrolyzable amide," "biohydrolyzable ester," "biohydrolyzable carbamate," "biohydrolyzable carbonate," "biohydrolyzable ureide," "biohydrolyzable phosphate" mean an amide, ester, carbamate, carbonate, ureide, or phosphate, respectively, of a compound that either: 1) does not interfere with the biological activity of the compound but can confer upon that compound advantageous properties in vivo, such as uptake, duration of action, or onset of action; or 2) is biologically inactive but is converted in vivo to the biologically active compound. Examples of biohydrolyzable esters include, but are not limited to, lower alkyl esters, lower acyloxyalkyl esters (such as acetoxylmethyl, acetoxyethyl, aminocarbonyloxymethyl, pivaloyloxymethyl, and pivaloyloxyethyl esters), lactonyl esters (such as phthalidyl and thiophthalidyl esters), lower alkoxyacyloxyalkyl esters (such as methoxycarbonyl-oxymethyl, ethoxycarbonyloxyethyl and isopropoxycarbonyloxyethyl esters), alkoxyalkyl esters, choline esters, and acylamino alkyl esters (such as acetamidomethyl esters). Examples of biohydrolyzable amides include, but are not limited to, lower alkyl amides, α-amino acid amides, alkoxyacyl amides, and alkylaminoalkylcarbonyl amides. Examples of biohydrolyzable carbamates include, but are not limited to, lower alkylamines, substituted ethylenediamines, amino acids, hydroxyalkylamines, heterocyclic and heteroaromatic amines, and polyether amines.

Various immunomodulatory compounds of the invention contain one or more chiral centers, and can exist as racemic mixtures of enantiomers or mixtures of diastereomers. This invention encompasses the use of stereomerically pure forms of such compounds, as well as the use of mixtures of those forms. For example, mixtures comprising equal or unequal amounts of the enantiomers of a particular immunomodulatory compounds of the invention may be used in methods and compositions of the invention. These isomers may be asymmetrically synthesized or resolved using standard techniques such as chiral columns or chiral resolving agents. See, e.g., Jacques, J., et al., *Enantiomers, Racemates and Resolutions* (Wiley-Interscience, New York, 1981); Wilen, S. H., et al., *Tetrahedron* 33:2725 (1977); Eliel, E. L., *Stereochemistry of Carbon Compounds* (McGraw-Hill, New York, 1962); and Wilen, S. H., *Tables of Resolving Agents and Optical Resolutions* p. 268 (E. L. Eliel, Ed., Univ. of Notre Dame Press, Notre Dame, Ind., 1972).

As used herein and unless otherwise indicated, the term "stereomerically pure" means a composition that comprises one stereoisomer of a compound and is substantially free of other stereoisomers of that compound. For example, a stereomerically pure composition of a compound having one chiral center will be substantially free of the opposite enantiomer of the compound. A stereomerically pure composition of a compound having two chiral centers will be substantially free of other diastereomers of the compound. A typical stereomerically pure compound comprises greater than about 80% by weight of one stereoisomer of the compound and less than about 20% by weight of other stereoisomers of the compound, more preferably greater than about 90% by weight of one stereoisomer of the compound and less than about 10% by weight of the other stereoisomers of the compound, even more preferably greater than about 95% by weight of one stereoisomer of the compound and less than about 5% by weight of the other stereoisomers of the compound, and most preferably greater than about 97% by weight of one stereoisomer of the compound and less than about 3% by weight of the other stereoisomers of the compound. As used herein and unless otherwise indicated, the term "stereomerically enriched" means a composition that comprises greater than about 60% by weight of one stereoisomer of a compound, preferably greater than about 70% by weight, more preferably greater than about 80% by weight of one stereoisomer of a compound. As used herein and unless otherwise indicated, the term "enantiomerically pure" means a stereomerically pure composition of a compound having one chiral center. Similarly, the term "enantiomerically enriched" means a stereomerically enriched composition of a compound having one chiral center.

It should be noted that if there is a discrepancy between a depicted structure and a name given that structure, the depicted structure is to be accorded more weight. In addition, if the stereochemistry of a structure or a portion of a structure is not indicated with, for example, bold or dashed lines, the structure or portion of the structure is to be interpreted as encompassing all stereoisomers of it.

4.2 Second Active Agents

A second active ingredient or agent can be used in the methods and compositions of the invention together with an immunomodulatory compound. In a preferred embodiment, the second active agents are capable of relieving pain, inhibiting inflammatory reactions, providing a sedative effect or an antineuralgic effect, or ensuring patient comfort.

Examples of the second active agents include, but are not limited to, opioid analgesics, non-narcotic analgesics, anti-inflammatories, cox-2 inhibitors, alpha-adrenergic receptor agonists or antagonists, ketamine, anesthetic agents, NMDA antagonists, immunomodulatory agents, immunosuppressive agents, antidepressants, anticonvulsants, antihypertensives, anxiolytics, calcium channel blockers, muscle relaxants, corticosteroids, hyperbaric oxygen, JNK inhibitors, other therapeutics known to relieve pain, and pharmaceutically acceptable salts, solvates, hydrates, stereoisomers, clathrates, prodrugs and pharmacologically active metabolites thereof.

Opioids can be used to treat severe pain. Examples of opioid analgesics include, but are not limited to, oxycodone (OxyContin®), morphine sulfate (MS Contin®, Duramorph®, Astramorph®), meperidine (Demerol®), and fentanyl transdermal patch (Duragesic®) and other known conventional medications; See, e.g., *Physicians' Desk Reference*, 594-595, 2851 and 2991 (57$^{th}$ ed., 2003). Oxycodone (OxyContin®) is a long-acting form of an opioid and may be used usually in initial and later stages of CRPS. Morphine sulfate may be used for analgesia due to reliable and predictable effects, safety profile, and ease of reversibility with naloxone. Morphine sulfate is sold in the United States under the trade name MS Contin®, Duramorph®, or Astramorph®. See, e.g., *Physicians' Desk Reference*, 594-595 (57$^{th}$ ed., 2003). Fentanyl transdermal patch (Duragesic®) is a potent narcotic analgesic with much shorter half-life than morphine sulfate. Meperidine (Demerol®) and hydromorphone (Dilaudid®) may also be used for pain management. See, e.g., *Physicians'Desk Reference*, 2991 (57$^{th}$ ed., 2003).

Non-narcotic analgesics and anti-inflammatories are preferably used for treatment of pain during pregnancy and breastfeeding. Anti-inflammatories such as non-steroidal anti-inflammatory drugs (NSAIDs) and cox-2 inhibitors typically inhibit inflammatory reactions and pain by decreasing the activity of cyclo-oxygenase, which is responsible for prostaglandin synthesis. NSAIDs may provide pain relief in the early stage of pain syndrome. Examples of anti-inflammatories include, but are not limited to, salicylic acid acetate (Aspirin®), ibuprofen (Motrin®, Advil®), ketoprofen (Oruvail®), rofecoxib (Vioxx®), naproxen sodium (Anaprox®, Naprelan®, Naprosyn®), ketorolac (Acular®), and other known conventional medications. A specific cox-2 inhibitor is celecoxib (Celebrex®). See, e.g., *Physicians' Desk Reference*, 1990, 1910-1914 and 2891 (57$^{th}$ ed., 2003); *Physicians' Desk Reference for Nonprescription Drugs and Dietary Supplements*, 511, 667 and 773 (23$^{rd}$ ed., 2002).

Antidepressants increase the synaptic concentration of serotonin and/or norepinephrine in the CNS by inhibiting their reuptake by presynaptic neuronal membrane. Some antidepressants also have sodium channel blocking ability to reduce the firing rate of injured peripheral afferent fibers. Examples of antidepressants include, but are not limited to, nortriptyline (Pamelor®), amitriptyline (Elavil®), imipramine (Tofranil®), doxepin (Sinequan®), clomipramine (Anafranil®), fluoxetine (Prozac®), sertraline (Zoloft®), nefazodone (Serzone®), venlafaxine (Effexor®), trazodone (Desyrel®), bupropion (Wellbutrin®) and other known conventional medications. See, e.g., *Physicians' Desk Reference,* 329, 1417, 1831 and 3270 (57th ed., 2003).

Anticonvulsant drugs may also be used in embodiments of the invention. Examples of anticonvulsants include, but are not limited to, carbamazepine, oxcarbazepine, gabapentin (Neurontin®), phenyloin, sodium valproate, clonazepam, topiramate, lamotrigine, zonisamide, and tiagabine. See, e.g., *Physicians' Desk Reference,* 2563 (57th ed., 2003).

Corticosteroids (e.g., prednisone, dexamethasone or hydrocortisone), orally active class Ib anti-arrhythmic agents (e.g., mexiletine), calcium channel blockers (e.g., nifedipine), beta-blockers (e.g., propranolol), alpha-blocker (e.g., phenoxybenzamine), and alpha2-adrenergic agonists (e.g., clonidine) can also be used in combination with an immunomodulatory compound. See, e.g., *Physicians' Desk Reference,* 1979, 2006 and 2190 (57th ed., 2003).

Specific second active agents used in the invention include, but are not limited to, salicylic acid acetate (Aspirin®), celecoxib (Celebrex®), Enbrel®, ketamine, gabapentin (Neurontin®), phenyloin (Dilantin®), carbamazepine (Tegretol®), oxcarbazepine (Trileptal®), valproic acid (Depakene®), morphine sulfate, hydromorphone, prednisone, griseofulvin, penthonium, alendronate, dyphenhydramide, guanethidine, ketorolac (Acular®), thyrocalcitonin, dimethylsulfoxide (DMSO), clonidine (Catapress®), bretylium, ketanserin, reserpine, droperidol, atropine, phentolamine, bupivacaine, lidocaine, acetaminophen, nortriptyline (Pamelor®), amitriptyline (Elavil®), imipramine (Tofranil®), doxepin (Sinequan®), clomipramine (Anafranil®), fluoxetine (Prozac®), sertraline (Zoloft®), nefazodone (Serzone®), venlafaxine (Effexor®), trazodone (Desyrel®), bupropion (Wellbutrin®), mexiletine, nifedipine, propranolol, tramadol, lamotrigine, ziconotide, ketamine, dextromethorphan, benzodiazepines, baclofen, tizanidine and phenoxybenzamine.

4.3 Methods of Treatment and Management

Methods of this invention encompass methods of preventing, treating, modifying and/or managing various types of pain. As used herein, unless otherwise specified, the term "preventing pain" includes, but is not limited to, inhibiting or reducing the severity of one or more symptoms associated with pain. Symptoms associated with pain include, but are not limited to, autonomic dysfunction, inability to initiate movement, weakness, tremor, muscle spasm, dytonia, dystrophy, atrophy, edema, stiffness, joint tenderness, increased sweating, sensitivity to temperature, light touch (allodynia), color change to the skin, hyperthermic or hypothermic, increased nail and hair growth, early bony changes, hyperhidrotic with livedo reticularis or cyanosis, lost hair, ridged, cracked or brittle nails, dry hand, diffuse osteoporosis, irreversible tissue damage, thin and shiny skin, joint contractures, and marked bone demineralization.

As used herein, unless otherwise specified, the term "treating pain" refers to the administration of a compound of the invention or other additional active agent after the onset of symptoms of pain, whereas "preventing" refers to the administration prior to the onset of symptoms, particularly to patients at risk of pain. Examples of patients at risk of pain include, but are not limited to, those who have incidents of trauma, neurologic disorder, myocardial infarction, musculoskeletal disorder and malignancy. Patients with familial history of pain syndromes are also preferred candidates for preventive regimens.

As used herein and unless otherwise indicated, the term "modifying pain" encompasses modulating the threshold, development and duration of pain, or changing the way that a patient responds to pain. Without being limited by theory, it is believed that an immunomodulatory compound can act as an antihyperalgesic and/or neuromodulator. In one embodiment, "modifying pain" encompasses removing exaggerated pain response of a patient (i.e., a level at which a patient experiences greater than normal pain in response to a particular stimulus) and taking the system of a human or animal back towards a normal pain threshold. In another embodiment, "modifying pain" encompasses reducing a patient's pain response to a stimulus of a particular intensity. In another embodiment, "modifying pain" encompasses increasing a patient's pain threshold relative to the patient's pain threshold prior to the administration of an effective amount of an immunomodulatory compound.

As used herein and unless otherwise indicated, the term "managing pain" encompasses preventing the recurrence of pain in a patient who had suffered from pain, and/or lengthening the time that a patient who/had suffered from pain remains in remission.

The invention encompasses methods of treating, preventing, modifying and managing pain syndromes in patients with various stages and specific types of the disease, including, but not limited to, those referred to as nociceptive pain, neuropathic pain, mixed pain of nociceptive and neuropathic pain, visceral pain, migraine headache and post-operative pain. Specific types of pain include, but are not limited to, pain associated with chemical or thermal burns, cuts of the skin, contusions of the skin, osteoarthritis, rheumatoid arthritis, or tendonitis, myofascial pain; CRPS type I, CRPS type II, reflex sympathetic dystrophy (RSD), reflex neurovascular dystrophy, reflex dystrophy, sympathetically maintained pain syndrome, causalgia, Sudeck atrophy of bone, algoneurodystrophy, shoulder hand syndrome, post-traumatic dystrophy, trigeminal neuralgia, post herpetic neuralgia, cancer related pain, phantom limb pain, fibromyalgia, chronic fatigue syndrome, spinal cord injury pain, central post-stroke pain, radiculopathy, diabetic neuropathy, post-stroke pain, luetic neuropathy, and other painful neuropathic conditions, e.g., painful neuropathic condition iatrogenically induced by drugs such as vincristine, velcade and thalidomide.

The invention further encompasses methods of treating, modifying or managing pain in patients who have been previously treated for pain but were not sufficiently responsive or were non-responsive to standard therapy, as well as those who have not previously been treated for pain. Because patients with pain have heterogeneous clinical manifestations and varying clinical outcomes, the treatment, modification or management given to a patient may vary, depending on his/her prognosis. The skilled clinician will be able to readily determine without undue experimentation specific secondary agents, types of surgery, and types of physical therapy that can be effectively used to treat an individual patient.

Methods encompassed by this invention comprise administering one or more immunomodulatory compounds, or a pharmaceutically acceptable salt, solvate, hydrate, stereoisomer, clathrate, or prodrug thereof to a patient (e.g., a human) suffering, or likely to suffer, from pain.

In one embodiment of the invention, an immunomodulatory compound is administered orally and in single or divided daily doses in an amount of from about 0.10 to about 150 mg/day. In a particular embodiment, 4-(amino)-2-(2,6 oxo(3-piperidyl))-isoindoline-1,3-dione is administered in an amount of from about 0.1 to 10 mg per day, or alternatively from about 0.1 to about 10 mg every other day or other syncopated regimen. In a preferred embodiment, 3-(4-amino-1-oxo-1,3-dihydro-isoindol-2-yl)-piperidine-2,6-dione is administered in an amount of from about 5 to 25 mg per day, or alternatively from about 5 to about 50 mg every other day or other syncopated regimen.

In one embodiment, the invention relates to a method for treating, preventing, managing and/or modifying nociceptive pain, comprising administering an effective amount of an immunomodulatory compound, or a pharmaceutically acceptable salt, solvate, hydrate, stereoisomer, clathrate, or prodrug thereof, to a patient in need thereof. In certain embodiments, the nociceptive pain results from physical trauma (e.g., a cut or contusion of the skin; or a chemical or thermal burn), osteoarthritis, rheumatoid arthritis, or tendonitis. In another embodiment, the nociceptive pain is myofascial pain.

In another embodiment, the invention relates to a method for treating, preventing, managing and/or modifying neuropathic pain, comprising administering an effective amount of an immunomodulatory compound, or a pharmaceutically acceptable salt, solvate, hydrate, stereoisomer, clathrate, or prodrug thereof, to a patient in need thereof. In certain embodiments, the neuropathic pain is associated with stroke, diabetic neuropathy, luetic neuropathy, postherpetic neuralgia, trigeminal neuralgia, or painful neuropathy induced iatrogenically from drugs such as vincristine, velcade or thalidomide.

In a further embodiment, the invention relates to a method for treating, preventing, managing and/or modifying mixed pain (i.e., pain with both nociceptive and neuropathic components), comprising administering an effective amount of an immunomodulatory compound, or a pharmaceutically acceptable salt, solvate, hydrate, stereoisomer, clathrate, or prodrug thereof, to a patient in need thereof.

Another embodiment of the invention comprises administering one or more immunomodulatory compounds, or a pharmaceutically acceptable salt, solvate, hydrate, stereoisomer, clathrate, or prodrug thereof, to a patient for treating, preventing, managing and/or modifying visceral pain, headache pain (e.g., migraine headache pain), CRPS type I, CRPS type II, RSD, reflex neurovascular dystrophy, reflex dystrophy, sympathetically maintained pain syndrome, causalgia, Sudeck atrophy of bone, algoneurodystrophy, shoulder hand syndrome, post-traumatic dystrophy, autonomic dysfunction, cancer-related pain, phantom limb pain, fibromyalgia, chronic fatigue syndrome, post-operative pain, spinal cord injury pain, central post-stroke pain, or radiculopathy.

In another embodiment, the invention relates to a method for treating, preventing, managing and/or modifying pain associated with a cytokine, comprising administering an effective amount of an immunomodulatory compound, or a pharmaceutically acceptable salt, solvate, hydrate, stereoisomer, clathrate, or prodrug thereof, to a patient in need thereof. In one embodiment, inhibiting cytokine activity or cytokine production results in the treatment, prevention, management and/or modification of the pain. In another embodiment, the cytokine is TNF-α. In another embodiment, the pain associated with a cytokine is nociceptive pain. In another embodiment, the pain associated with a cytokine is neuropathic pain.

In another embodiment, the invention relates to a method for treating, preventing, managing and/or modifying pain associated with inflammation, comprising administering an effective amount of an immunomodulatory compound, or a pharmaceutically acceptable salt, solvate, hydrate, stereoisomer, clathrate, or prodrug thereof, to a patient in need thereof.

In another embodiment, the invention relates to a method for treating, preventing, managing and/or modifying pain associated with a mitogen-activated protein kinase (MAPK), comprising administering an effective amount of an immunomodulatory compound to a patient in need thereof. In one embodiment, the MAPK is JNK (e.g., JNK1, JNK2 or JNK3). In another embodiment, the MAPK is an extracellular signal-regulated kinase (IRK) (e.g., ERK1 or ERK2).

In another embodiment, the invention relates to a method of treating, preventing, managing and/or modifying pain associated with surgery, in one embodiment planned surgery (i.e., planned trauma), comprising administering an effective amount of an immunomodulatory compound to a patient in need thereof. In this embodiment, the immunomodulatory compound can be administered before, during and/or after the planned surgery. In a particular embodiment, the patient is administered with about 5 to about 25 mg/day of an immunomodulatory compound from about 1-21 days prior to the planned surgery and/or about 5 to about 25 mg/day of an immunomodulatory compound from about 1-21 days after the planned surgery. In another embodiment, the patient is administered with about 10 mg/day of an immunomodulatory compound from about 1-21 days prior to the planned surgery and/or about 10 mg/day of an immunomodulatory compound from about 1-21 days after the planned surgery.

4.3.1 Combination Therapy With A Second Active Agent

Specific methods of the invention comprise administering an immunomodulatory compound, or a pharmaceutically acceptable salt, solvate, hydrate, stereoisomer, clathrate, or prodrug thereof, in combination with a second active agent or active ingredient. Examples of immunomodulatory compounds are disclosed herein (see, e.g., section 4.1); and examples of second active agents are also disclosed herein (see, e.g., section 4.2).

Administration of the immunomodulatory compounds and the second active agents to a patient can occur simultaneously or sequentially by the same or different routes of administration. The suitability of a particular route of administration employed for a particular active agent will depend on the active agent itself (e.g., whether it can be administered orally without decomposing prior to entering the blood stream) and the disease being treated. A preferred route of administration for immunomodulatory compounds is oral. Preferred routes of administration for the second active agents or ingredients of the invention are known to those of ordinary skill in the art. See, e.g., *Physicians' Desk Reference*, 594-597 (57$^{th}$ ed., 2003).

In one embodiment, the second active agent is administered orally, intravenously, intramuscularly, subcutaneously, mucosally, or transdermally and once or twice daily in an amount of from about 1 to about 3,500 mg, from about 5 to about 2,500 mg, from about 10 to about 500 mg, or from about 25 to about 250 mg.

The specific amount of the second active agent will depend on the specific agent used, the type of pain being treated or managed, the severity and stage of pain, and the amount(s) of immunomodulatory compounds and any optional additional active agents concurrently administered to the patient. In a particular embodiment, the second active agent is salicylic acid acetate (Aspirin®), celecoxib (Celebrex®), Enbrel®, Remicade®, Humira®, Kineret®, ketamine, gabapentin (Neurontin®), phenyloin (Dilantin®), carbamazepine (Tegretol®), oxcarbazepine (Trileptal®), valproic acid (Depakene®), morphine sulfate, hydromorphone, prednisone, griseofulvin, penthonium, alendronate, dyphenhydramide, guanethidine, ketorolac (Acular®), thyrocalcitonin, dimethylsulfoxide (DMSO), clonidine (Catapress®), bretylium, ketanserin, reserpine, droperidol, atropine, phentolamine, bupivacaine, lidocaine, acetaminophen, nortriptyline (Pamelor®), amitriptyline (Elavil®), imipramine (Tofranil®), doxepin (Sinequan®), clomipramine (Anafranil®), fluoxetine (Prozac®), sertraline (Zoloft®), nefazodone (Serzone®), venlafaxine (Effexor®), trazodone (Desyrel®), bupropion (Wellbutrin®), mexiletine, nifedipine, propranolol, tramadol, lamotrigine, ziconotide, ketamine, dextromethorphan, benzodiazepines, baclofen, tizanidine, phenoxybenzamine or a combination thereof, or a pharmaceutically acceptable salt, solvate, hydrate, stereoisomer, clathrate, prodrug or pharmacologically active metabolite thereof.

Hydromorphone (Dilaudid®) is preferably administered in an initial dose of about 2 mg orally, or about 1 mg intravenously to manage moderate to severe pain. See, e.g., *Physicians' Desk Reference*, 2991 (57$^{th}$ ed., 2003). Morphine sulphate (Duramorph®, Astramorph®, MS Contin®) is preferably administered in an initial dose of about 2 mg IV/SC/IM, depending on whether a patient has already taken narcotic analgesics. See, e.g., *Physicians' Desk Reference*, 594-595 (57$^{th}$ ed., 2003). No intrinsic limit to the amount that can be given exists, as long as a patient is observed for signs of adverse effects, especially respiratory depression. Various IV doses may be used, commonly titrated until a desired effect is obtained. For patients not using long-term agents, as little as 2 mg IV/SC may be sufficient. Larger doses are typically required for patients taking long-term narcotic analgesics. Morphine sulphate are also available in oral form in immediate-release and timed-release preparations. The long-acting oral form may be administered twice per day. An immediate-release form may be needed for periods of pain break-through, with the dose dependent on previous use. Oxycodone (OxyContin®) is a long-acting form of an opioid and may be used in initial and later stages of pain syndrome. Oxycodone (OxyContin®) is preferably administered in an amount of about 10-160 mg twice a day. See, e.g., *Physicians' Desk Reference*, 2851 (57$^{th}$ ed., 2003). Meperidine (Demerol®) is preferably administered in an amount of about 50-150 mg PO/IV/IM/SC every 3-4 hours. A typical pediatric dose of meperidine (Demerol®) is 1-1.8 mg/kg (0.5-0.8 mg/lb) PO/IV/IM/SC every 3-4 hours. See, e.g., *Physicians' Desk Reference*, 2991 (57$^{th}$ ed., 2003). Fentanyl transdermal patch (Duragesic®) is available as a transdermal dosage form. Most patients are administered the drug in 72 hour dosing intervals; however, some patients may require dosing intervals of about 48 hours. A typical adult dose is about 25 mcg/h (10 cm$^2$), 50 mcg/h (20 cm$^2$), 75 mcg/h (75 cm$^2$), or 100 mcg/h (100 cm$^2$). See, e.g., *Physicians' Desk Reference*, 1775 (57$^{th}$ ed., 2003).

Non-narcotic analgesics and anti-inflammatories such as NSAIDs and cox-2 inhibitors may be used to treat patients suffering from mild to moderate pain. Ibuprofen (Motrin®, Advil®) is orally administered in an amount of 400-800 mg three times a day. See, e.g., *Physicians' Desk Reference*, 1900-1904 (57$^{th}$ ed., 2003); *Physicians' Desk Reference for Nonprescription Drugs and Dietary Supplements*, 511, 667 and 773 (23$^{rd}$ ed., 2002). Naproxen sodium (Anaprox®, Naprelan®, Naprosyn®) may also preferably be used for relief of mild to moderate pain in an amount of about 275 mg thrice a day or about 550 mg twice a day. See, e.g., *Physicians' Desk Reference*, 1417, 2193 and 2891 (57$^{th}$ ed., 2003).

Antidepressants, e.g., nortriptyline (Pamelor®), may also be used in embodiments of the invention to treat patients suffering from chronic and/or neuropathic pain. The oral adult dose is typically in an amount of about 25-100 mg, and preferably does not exceed 200 mg/d. A typical pediatric dose is about 0.1 mg/kg PO as initial dose, increasing, as tolerated, up to about 0.5-2 mg/d. Amitriptyline (Etrafon®) is preferably used for neuropathic pain in an adult dose of about 25-100 mg PO. See, e.g. *Physicians' Desk Reference*, 1417 and 2193 (57$^{th}$ ed., 2003).

Anticonvulsants such as gabapentin (Neurontin®) may also be used to treat patients suffering from chronic and neuropathic pain. Preferably, gabapentin is orally administered in an amount of about 100-1,200 mg three times a day. See, e.g., *Physicians' Desk Reference*, 2563 (57$^{th}$ ed., 2003). Carbamazepine (Tegretol®) is used to treat pain associated with true trigeminal neuralgia. The oral adult dose is typically in an amount of about 100 mg twice a day as initial dose, increasing, as tolerated, up to about 2,400 mg/d. See, e.g., *Physicians' Desk Reference*, 2323-25 (57$^{th}$ ed., 2003).

In one embodiment, an immunomodulatory compound and a second active agent are administered to a patient, preferably a mammal, more preferably a human, in a sequence and within a time interval such that the immunomodulatory compound can act together with the other agent to provide an increased benefit than if they were administered otherwise. For example, the second active agent can be administered at the same time or sequentially in any order at different points in time; however, if not administered at the same time, they should be administered sufficiently close in time so as to provide the desired therapeutic or prophylactic effect. In one embodiment, the immunomodulatory compound and the second active agent exert their effect at times which overlap. Each second active agent can be administered separately, in any appropriate form and by any suitable route. In other embodiments, the immunomodulatory compound is administered before, concurrently or after administration of the second active agent. Surgery can also be performed as a preventive measure or to relieve pain.

In various embodiments, the immunomodulatory compound and the second active agent are administered less than about 1 hour apart, at about 1 hour apart, at about 1 hour to about 2 hours apart, at about 2 hours to about 3 hours apart, at about 3 hours to about 4 hours apart, at about 4 hours to about 5 hours apart, at about 5 hours to about 6 hours apart, at about 6 hours to about 7 hours apart, at about 7 hours to about 8 hours apart, at about 8 hours to about 9 hours apart, at about 9 hours to about 10 hours apart, at about 10 hours to about 11 hours apart, at about 11 hours to about 12 hours apart, no more than 24 hours apart or no more than 48 hours apart. In other embodiments, the immunomodulatory compound and the second active agent are administered concurrently.

In other embodiments, the immunomodulatory compound and the second active agent are administered at about 2 to 4 days apart, at about 4 to 6 days apart, at about 1 week part, at about 1 to 2 weeks apart, or more than 2 weeks apart.

In certain embodiments, the immunomodulatory compound and optionally the second active agent are cyclically administered to a patient. Cycling therapy involves the administration of a first agent for a period of time, followed by the administration of a second agent and/or third agent for a period of time and repeating this sequential administration. Cycling therapy can reduce the development of resistance to one or more of the therapies, avoid or reduce the side effects of one of the therapies, and/or improve the efficacy of the treatment.

In certain embodiments, the immunomodulatory compound and optionally the second active agent are administered in a cycle of less than about 3 weeks, about once every two weeks, about once every 10 days or about once every week. One cycle can comprise the administration of an immunomodulatory compound and optionally the second active agent by infusion over about 90 minutes every cycle, about 1 hour every cycle, about 45 minutes every cycle. Each cycle can comprise at least 1 week of rest, at least 2 weeks of rest, at least 3 weeks of rest. The number of cycles administered is from about 1 to about 12 cycles, more typically from about 2 to about 10 cycles, and more typically from about 2 to about 8 cycles.

In yet other embodiments, the immunomodulatory compound is administered in metronomic dosing regimens, either by continuous infusion or frequent administration without extended rest periods. Such metronomic administration can involve dosing at constant intervals without rest periods. Typically the immunomodulatory compounds, are used at lower doses. Such dosing regimens encompass the chronic daily administration of relatively low doses for extended periods of time. In preferred embodiments, the use of lower doses can minimize toxic side effects and eliminate rest periods. In certain embodiments, the immunomodulatory compound is delivered by chronic low-dose or continuous infusion ranging from about 24 hours to about 2 days, to about 1 week, to about 2 weeks, to about 3 weeks to about 1 month to about 2 months, to about 3 months, to about 4 months, to about 5 months, to about 6 months. The scheduling of such dose regimens can be optimized by the skilled artisan.

In other embodiments, courses of treatment are administered concurrently to a patient, i.e., individual doses of the second active agent are administered separately yet within a time interval such that the immunomodulatory compound can work together with the second active agent. For example, one component can be administered once per week in combination with the other components that can be administered once every two weeks or once every three weeks. In other words, the dosing regimens are carried out concurrently even if the therapeutics are not administered simultaneously or during the same day.

The second active agent can act additively or, more preferably, synergistically with the immunomodulatory compound. In one embodiment, an immunomodulatory compound is administered concurrently with one or more second active agents in the same pharmaceutical composition. In another embodiment, an immunomodulatory compound is administered concurrently with one or more second active agents in separate pharmaceutical compositions. In still another embodiment, an immunomodulatory compound is administered prior to or subsequent to administration of a second active agent. The invention contemplates administration of an immunomodulatory compound and a second active agent by the same or different routes of administration, e.g., oral and parenteral. In certain embodiments, when an immunomodulatory compound is administered concurrently with a second active agent that potentially produces adverse side effects including, but not limited to, toxicity, the second active agent can advantageously be administered at a dose that falls below the threshold that the adverse side effect is elicited.

4.3.2 Use With Pain Management Interventional Techniques

In still another embodiment, this invention encompasses a method of treating, preventing, modifying and/or managing pain, which comprises administering an immunomodulatory compound, or a pharmaceutically acceptable salt, solvate, hydrate, stereoisomer, clathrate, or prodrug thereof, in conjunction with (e.g. before, during, or after) Pain Management interventional techniques. Examples of Pain Management interventional techniques include, but are not limited to, the use of sympathetic blocks, intravenous regional blocks, placement of dorsal column stimulators or placement of intrathecal infusion devices for analgesic medication delivery. Preferred Pain Management interventional techniques provides a selective neural blockade which interrupts the activity of the sympathetic nervous system in the region affected by pain.

The combined use of the immunomodulatory compounds and Pain Management interventional techniques may provide a unique treatment regimen that is unexpectedly effective in certain patients. Without being limited by theory, it is believed that immunomodulatory compounds may provide additive or synergistic effects when given concurrently with Pain Management interventional techniques. An example of Pain Management interventional techniques is intravenous regional block using BIER block with a variety of agents such as, but not limited to, local anesthetics such as, bupivacaine and lidocaine, guanethidine, ketamine, bretylium, steroids, ketorolac, and reserpine. Perez R. S., et al., *J Pain Symptom Manage* 2001 June; 21(6): 511-26. For CRPS cases involving the upper extremities, a stellate (cervicothoracic) ganglion block may be used. The invention also encompasses the use of a somatic block, which involves continuous epidural infusion along with different variants of brachial plexus blocks. An axillary, supraclavicular, or infraclavicular approach of the somatic block may also be useful.

4.3.3 Use With Physical Therapy or Psychological Therapy

In still another embodiment, this invention encompasses a method of treating, preventing, modifying and/or managing pain, which comprises administering an immunomodulatory compound, or a pharmaceutically acceptable salt, solvate, hydrate, stereoisomer, clathrate, or prodrug thereof, in conjunction with physical therapy or psychological therapy.

As described above, symptoms of pain include vasomotor dysfunction and movement disorders. A steady progression of gentle weight bearing to progressive active weight bearing is very important in patients with pain syndromes. Gradual desensitization to increasing sensory stimuli may also be helpful. Gradual increase in normalized sensation tends to reset the altered processing in the CNS. Physical therapy can thus play an important role in functional restoration. The goal of physical therapy is to gradually increase strength and flexibility.

It is believed that the combined use of the immunomodulatory compounds and physical therapy may provide a unique treatment regimen that is unexpectedly effective in certain patients. Without being limited by theory, it is believed that immunomodulatory compounds may provide additive or synergistic effects when given concurrently with physical therapy.

Much pain literature notes a concomitant behavioral and psychiatric morbidities such as depression and anxiety. It is believed that the combined use of the immunomodulatory compounds and psychological treatment may provide a unique treatment regimen that is unexpectedly effective in certain patients. Without being limited by theory, it is believed that immunomodulatory compounds may provide additive or synergistic effects when given concurrently with psychological therapy including, but not limited to, biofeedback, relaxation training, cognitive-behavioral therapy, and individual or family psychotherapy.

The immunomodulatory compound, or a pharmaceutically acceptable salt, solvate, hydrate, stereoisomer, clathrate, or prodrug thereof is administered before, during, or after physical therapy or psychological treatment. In specific methods, a second active agent is also administered to the patient.

4.4 Pharmaceutical Compositions and Single Unit Dosage Forms

Pharmaceutical compositions can be used in the preparation of individual, single unit dosage forms. Pharmaceutical compositions and dosage forms of the invention comprise immunomodulatory compounds, or a pharmaceutically acceptable salt, solvate, hydrate, stereoisomer, clathrate, or prodrug thereof. Pharmaceutical compositions and dosage forms of the invention can further comprise one or more excipients.

Pharmaceutical compositions and dosage forms of the invention can also comprise one or more additional active ingredients. Consequently, pharmaceutical compositions and dosage forms of the invention comprise the active agents disclosed herein (e.g., immunomodulatory compounds, or a pharmaceutically acceptable salt, solvate, hydrate, stereoisomer, clathrate, or prodrug thereof, and a second active agent). Examples of optional additional active agents are disclosed herein (see, e.g., section 4.2).

Single unit dosage forms of the invention are suitable for oral, mucosal (e.g., nasal, sublingual, vaginal, buccal, or rectal), or parenteral (e.g., subcutaneous, intravenous, bolus injection, intramuscular, or intraarterial), transdermal or transcutaneous administration to a patient. Examples of dosage forms include, but are not limited to: tablets; caplets; capsules, such as soft elastic gelatin capsules; cachets; troches; lozenges; dispersions; suppositories; powders; aerosols (e.g., nasal sprays or inhalers); gels; liquid dosage forms suitable for oral or mucosal administration to a patient, including suspensions (e.g., aqueous or non-aqueous liquid suspensions, oil-in-water emulsions, or a water-in-oil liquid emulsions), solutions, and elixirs; liquid dosage forms suitable for parenteral administration to a patient; and sterile solids (e.g., crystalline or amorphous solids) that can be reconstituted to provide liquid dosage forms suitable for parenteral administration to a patient.

The composition, shape, and type of dosage forms of the invention will typically vary depending on their use. For example, a dosage form used in the acute treatment of a disease may contain larger amounts of one or more of the active agents it comprises than a dosage form used in the chronic treatment of the same disease. Similarly, a parenteral dosage form may contain smaller amounts of one or more of the active agents it comprises than an oral dosage form used to treat the same disease. These and other ways in which specific dosage forms encompassed by this invention will vary from one another will be readily apparent to those skilled in the art. See, e.g., *Remington's Pharmaceutical Sciences*, 18th ed., Mack Publishing, Easton Pa. (1990).

Typical pharmaceutical compositions and dosage forms comprise one or more excipients. Suitable excipients are well known to those skilled in the art of pharmacy, and non-limiting examples of suitable excipients are provided herein. Whether a particular excipient is suitable for incorporation into a pharmaceutical composition or dosage form depends on a variety of factors well known in the art including, but not limited to, the way in which the dosage form will be administered to a patient. For example, oral dosage forms such as tablets may contain excipients not suited for use in parenteral dosage forms. The suitability of a particular excipient may also depend on the specific active ingredients in the dosage form. For example, the decomposition of some active ingredients may be accelerated by some excipients such as lactose, or when exposed to water. Active ingredients that comprise primary or secondary amines are particularly susceptible to such accelerated decomposition. Consequently, this invention encompasses pharmaceutical compositions and dosage forms that contain little, if any, lactose other mono- or disaccharides. As used herein, the term "lactose-free" means that the amount of lactose present, if any, is insufficient to substantially increase the degradation rate of an active ingredient.

Lactose-free compositions of the invention can comprise excipients that are well known in the art and are listed, for example, in the *U.S. Pharmacopeia* (ASP) 25-NF20 (2002). In general, lactose-free compositions comprise active ingredients, a binder/filler, and a lubricant in pharmaceutically compatible and pharmaceutically acceptable amounts. Preferred lactose-free dosage forms comprise active ingredients, microcrystalline cellulose, pre-gelatinized starch, and magnesium stearate.

This invention further encompasses anhydrous pharmaceutical compositions and dosage forms comprising active ingredients, since water can facilitate the degradation of some compounds. For example, the addition of water (e.g., 5%) is widely accepted in the pharmaceutical arts as a means of simulating long-term storage in order to determine characteristics such as shelf-life or the stability of formulations over time. See, e.g., Jens T. Carstensen, *Drug Stability: Principles & Practice*, 2d. Ed., Marcel Dekker, NY, N.Y., 1995, pp. 379-80. In effect, water and heat accelerate the decomposition of some compounds. Thus, the effect of water on a formulation can be of great significance since moisture and/or humidity are commonly encountered during manufacture, handling, packaging, storage, shipment, and use of formulations.

Anhydrous pharmaceutical compositions and dosage forms of the invention can be prepared using anhydrous or low moisture containing ingredients and low moisture or low humidity conditions. Pharmaceutical compositions and dosage forms that comprise lactose and at least one active ingredient that comprises a primary or secondary amine are preferably anhydrous if substantial contact with moisture and/or humidity during manufacturing, packaging, and/or storage is expected.

An anhydrous pharmaceutical composition should be prepared and stored such that its anhydrous nature is maintained. Accordingly, anhydrous compositions are preferably packaged using materials known to prevent exposure to water such that they can be included in suitable formulary kits. Examples of suitable packaging include, but are not limited to, hermetically sealed foils, plastics, unit dose containers (e.g., vials), blister packs, and strip packs.

The invention further encompasses pharmaceutical compositions and dosage forms that comprise one or more compounds that reduce the rate by which an active ingredient will decompose. Such compounds, which are referred to herein as "stabilizers," include, but are not limited to, antioxidants such as ascorbic acid, pH buffers, or salt buffers.

Like the amounts and types of excipients, the amounts and specific types of active ingredients in a dosage form may differ depending on factors such as, but not limited to, the route by which it is to be administered to patients. However, typical dosage forms of the invention comprise immunomodulatory compounds or a pharmaceutically acceptable salt, solvate, hydrate, stereoisomer, clathrate, or prodrug thereof, in an amount of from about 0.10 to about 150 mg. Typical dosage forms comprise immunomodulatory compounds or a pharmaceutically acceptable salt, solvate, hydrate, stereoisomer, clathrate, or prodrug thereof, in an amount of about 0.1, 1, 2, 5, 7.5, 10, 12.5, 15, 17.5, 20, 25, 50, 100, 150 or 200 mg. In a particular embodiment, a preferred dosage form comprises 4-(amino)-2-(2,6-dioxo(3-piperidyl))-isoindoline-1,3-one in an amount of about 1, 2, 5, 10, 25 or 50 mg. In a specific embodiment, a preferred dosage form comprises 3-(4-amino-1-oxo-1,3-dihydro-isoindol-2-yl)-piperidine-2,6-dione in an amount of about 5, 10, 25 or 50 mg. Typical dosage forms comprise the second active agent in an amount of form about 1 to about 3,500 mg, from about 5 to about 2,500 mg, from about 10 to about 500 mg, or from about 25 to about 250 mg. Of course, the specific amount of the second active agent will depend on the specific agent used, the type of pain being treated or managed, and the amount(s) of immunomodulatory compounds and any optional additional active agents concurrently administered to the patient.

4.4.1 Oral Dosage Forms

Pharmaceutical compositions of the invention that are suitable for oral administration can be presented as discrete dosage forms, such as, but are not Limited to, tablets (e.g., chewable tablets), caplets, capsules, and liquids (e.g., flavored syrups). Such dosage forms contain predetermined amounts of active agents, and may be prepared by methods of pharmacy well known to those skilled in the art. See generally, *Remington's Pharmaceutical Sciences,* 18th ed., Mack Publishing, Easton Pa. (1990).

Typical oral dosage forms of the invention are prepared by combining the active ingredients in an intimate admixture with at least one excipient according to conventional pharmaceutical compounding techniques. Excipients can take a wide variety of forms depending on the form of preparation desired for administration. For example, excipients suitable for use in oral liquid or aerosol dosage forms include, but are not limited to, water, glycols, oils, alcohols, flavoring agents, preservatives, and coloring agents. Examples of excipients suitable for use in solid oral dosage forms (e.g., powders, tablets, capsules, and caplets) include, but are not limited to, starches, sugars, micro-crystalline cellulose, diluents, granulating agents, lubricants, binders, and disintegrating agents.

Because of their ease of administration, tablets and capsules represent the most advantageous oral dosage unit forms, in which case solid excipients are employed. If desired, tablets can be coated by standard aqueous or nonaqueous techniques. Such dosage forms can be prepared by any of the methods of pharmacy. In general, pharmaceutical compositions and dosage forms are prepared by uniformly and intimately admixing the active ingredients with liquid carriers, finely divided solid carriers, or both, and then shaping the product into the desired presentation if necessary.

For example, a tablet can be prepared by compression or molding. Compressed tablets can be prepared by compressing in a suitable machine the active ingredients in a free-flowing form such as powder or granules, optionally mixed with an excipient. Molded tablets can be made by molding in a suitable machine a mixture of the powdered compound moistened with an inert liquid diluent.

Examples of excipients that can be used in oral dosage forms of the invention include, but are not limited to, binders, fillers, disintegrants, and lubricants. Binders suitable for use in pharmaceutical compositions and dosage forms include, but are not limited to, corn starch, potato starch, or other starches, gelatin, natural and synthetic gums such as acacia, sodium alginate, alginic acid, other alginates, powdered tragacanth, guar gum, cellulose and its derivatives (e.g., ethyl cellulose, cellulose acetate, carboxymethyl cellulose calcium, sodium carboxymethyl cellulose), polyvinyl pyrrolidone, methyl cellulose, pre-gelatinized starch, hydroxypropyl methyl cellulose, (e.g., Nos. 2208, 2906, 2910), microcrystalline cellulose, and mixtures thereof.

Suitable forms of microcrystalline cellulose include, but are not limited to, the materials sold as AVICEL-PH-101, AVICEL-PH-103 AVICEL RC-581, AVICEL-PH-105 (available from FMC Corporation, American Viscose Division, Avicel Sales, Marcus Hook, Pa.), and mixtures thereof. An specific binder is a mixture of microcrystalline cellulose and sodium carboxymethyl cellulose sold as AVICEL RC-581. Suitable anhydrous or low moisture excipients or additives include AVICEL-PH-103™ and Starch 1500 LM.

Examples of fillers suitable for use in the pharmaceutical compositions and dosage forms disclosed herein include, but are not limited to, talc, calcium carbonate (e.g. granules or powder), microcrystalline cellulose, powdered cellulose, dextrates, kaolin, mannitol, silicic acid, sorbitol, starch, pre-gelatinized starch, and mixtures thereof. The binder or filler in pharmaceutical compositions of the invention is typically present in from about 50 to about 99 weight percent of the pharmaceutical composition or dosage form.

Disintegrants are used in the compositions of the invention to provide tablets that disintegrate when exposed to an aqueous environment. Tablets that contain too much disintegrant may disintegrate in storage, while those that contain too little may not disintegrate at a desired rate or under the desired conditions. Thus, a sufficient amount of disintegrant that is neither too much nor too little to detrimentally alter the release of the active ingredients should be used to form solid oral dosage forms of the invention. The amount of disintegrant used varies based upon the type of formulation, and is readily discernible to those of ordinary skill in the art. Typical pharmaceutical compositions comprise from about 0.5 to about 15 weight percent of disintegrant, preferably from about 1 to about 5 weight percent of disintegrant.

Disintegrants that can be used in pharmaceutical compositions and dosage forms of the invention include, but are not limited to, agar-agar, alginic acid, calcium carbonate, microcrystalline cellulose, croscarmellose sodium, crospovidone, polacrilin potassium, sodium starch glycolate, potato or tapioca starch, other starches, pre-gelatinized starch, other starches, clays, other algins, other celluloses, gums, and mixtures thereof.

Lubricants that can be used in pharmaceutical compositions and dosage forms of the invention include, but are not limited to, calcium stearate, magnesium stearate, mineral oil, light mineral oil, glycerin, sorbitol, mannitol, polyethylene glycol, other glycols, stearic acid, sodium lauryl sulfate, talc, hydrogenated vegetable oil (e.g., peanut oil, cottonseed oil, sunflower oil, sesame oil, olive oil, corn oil, and soybean oil), zinc stearate, ethyl oleate, ethyl laureate, agar, and mixtures thereof. Additional lubricants include, for example, a syloid silica gel (AEROSIL200, manufactured by W.R. Grace Co. of Baltimore, Md.), a coagulated aerosol of synthetic silica (marketed by Degussa Co. of Plano, Tex.), CAB-O-SIL (a pyrogenic silicon dioxide product sold by Cabot Co. of Boston, Mass.), and mixtures thereof. If used at all, lubricants are typically used in an amount of less than about 1 weight percent of the pharmaceutical compositions or dosage forms into which they are incorporated.

A preferred solid oral dosage form of the invention comprises immunomodulatory compounds, anhydrous lactose, microcrystalline cellulose, polyvinylpyrrolidone, stearic acid, colloidal anhydrous silica, and gelatin.

4.4.2 Delayed Release Dosage Forms

Active agents of the invention can be administered by controlled release means or by delivery devices that are well known to those of ordinary skill in the art. Examples include, but are not limited to, those described in U.S. Pat. Nos. 3,845, 770; 3,916,899; 3,536,809; 3,598,123; and 4,008,719, 5,674, 533, 5,059,595, 5,591,767, 5,120,548, 5,073,543, 5,639,476, 5,354,556, and 5,733,566, each of which is incorporated herein by reference. Such dosage forms can be used to provide slow or controlled-release of one or more active ingredients using, for example, hydropropylmethyl cellulose, other polymer matrices, gels, permeable membranes, osmotic systems, multilayer coatings, microparticles, liposomes, microspheres, or a combination thereof to provide the desired release profile in varying proportions. Suitable controlled-release formulations known to those of ordinary skill in the art, including those described herein, can be readily selected for use with the active ingredients of the invention. The invention thus encompasses single unit dosage forms suitable for oral administration such as, but not limited to, tablets, capsules, gelcaps, and caplets that are adapted for controlled-release.

All controlled-release pharmaceutical products have a common goal of improving drug therapy over that achieved by their non-controlled counterparts. Ideally, the use of an optimally designed controlled-release preparation in medical treatment is characterized by a minimum of drug substance being employed to cure or control the condition in a minimum amount of time. Advantages of controlled-release formulations include extended activity of the drug, reduced dosage frequency, and increased patient compliance. In addition, controlled-release formulations can be used to affect the time of onset of action or other characteristics, such as blood levels of the drug, and can thus affect the occurrence of side (e.g., adverse) effects.

Most controlled-release formulations are designed to initially release an amount of drug (active ingredient) that promptly produces the desired therapeutic effect, and gradually and continually release of other amounts of drug to maintain this level of therapeutic or prophylactic effect over an extended period of time. In order to maintain this constant level of drug in the body, the drug must be released from the dosage form at a rate that will replace the amount of drug being metabolized and excreted from the body. Controlled-release of an active ingredient can be stimulated by various conditions including, but not limited to, pH, temperature, enzymes, water, or other physiological conditions or compounds.

4.4.3 Parenteral Dosage Forms

Parenteral dosage forms can be administered to patients by various routes including, but not limited to, subcutaneous, intravenous (including bolus injection), intramuscular, and intraarterial. Because their administration typically bypasses patients' natural defenses against contaminants, parenteral dosage forms are preferably sterile or capable of being sterilized prior to administration to a patient. Examples of parenteral dosage forms include, but are not limited to, solutions ready for injection, dry products ready to be dissolved or suspended in a pharmaceutically acceptable vehicle for injection, suspensions ready for injection, and emulsions.

Suitable vehicles that can be used to provide parenteral dosage forms of the invention are well known to those skilled in the art. Examples include, but are not limited to: Water for Injection USP; aqueous vehicles such as, but not limited to, Sodium Chloride Injection, Ringer's Injection, Dextrose Injection, Dextrose and Sodium Chloride Injection, and Lactated Ringer's Injection; water-miscible vehicles such as, but not limited to, ethyl alcohol, polyethylene glycol, and polypropylene glycol; and non-aqueous vehicles such as, but not limited to, corn oil, cottonseed oil, peanut oil, sesame oil, ethyl oleate, isopropyl myristate, and benzyl benzoate.

Compounds that increase the solubility of one or more of the active ingredients disclosed herein can also be incorporated into the parenteral dosage forms of the invention. For example, cyclodextrin and its derivatives can be used to increase the solubility of immunomodulatory compounds and its derivatives. See, e.g., U.S. Pat. No. 5,134,127, which is incorporated herein by reference.

4.4.4 Topical and Mucosal Dosage Forms

Topical and mucosal dosage forms of the invention include, but are not limited to, sprays, aerosols, solutions, emulsions, suspensions, or other forms known to one of skill in the art. See, e.g., *Remington's Pharmaceutical Sciences*, $16^{th}$ and $18^{th}$ eds., Mack Publishing, Easton Pa. (1980 & 1990); and Introduction to Pharmaceutical Dosage Forms, 4th ed., Lea & Febiger, Philadelphia (1985). Dosage forms suitable for treating mucosal tissues within the oral cavity can be formulated as mouthwashes or as oral gels.

Suitable excipients (e.g., carriers and diluents) and other materials that can be used to provide topical and mucosal dosage forms encompassed by this invention are well known to those skilled in the pharmaceutical arts, and depend on the particular tissue to which a given pharmaceutical composition or dosage form will be applied. With that fact in mind, typical excipients include, but are not limited to, water, acetone, ethanol, ethylene glycol, propylene glycol, butane-1,3-diol, isopropyl myristate, isopropyl palmitate, mineral oil, and mixtures thereof to form solutions, emulsions or gels, which are non-toxic and pharmaceutically acceptable. Moisturizers or humectants can also be added to pharmaceutical compositions and dosage forms if desired. Examples of such additional ingredients are well known in the art. See, e.g., *Remington's Pharmaceutical Sciences*, $16^{th}$ and $18^{th}$ eds., Mack Publishing, Easton Pa. (1980 & 1990).

The pH of a pharmaceutical composition or dosage form may also be adjusted to improve delivery of one or more active ingredients. Similarly, the polarity of a solvent carrier, its ionic strength, or tonicity can be adjusted to improve delivery. Compounds such as stearates can also be added to pharmaceutical compositions or dosage forms to advantageously alter the hydrophilicity or lipophilicity of one or more active ingredients so as to improve delivery. In this regard, stearates can serve as a lipid vehicle for the formulation, as an emulsifying agent or surfactant, and as a delivery-enhancing or penetration-enhancing agent. Different salts, hydrates or solvates of the active ingredients can be used to further adjust the properties of the resulting composition.

4.4.5 Kits

Typically, active ingredients of the invention are preferably not administered to a patient at the same time or by the same route of administration. This invention therefore encompasses kits which, when used by the medical practitioner, can simplify the administration of appropriate amounts of active ingredients to a patient.

A typical kit of the invention comprises a dosage form of immunomodulatory compounds, or a pharmaceutically acceptable salt, solvate, hydrate, stereoisomer; prodrug, or clathrate thereof. Kits encompassed by this invention can further comprise additional active ingredients or a combination thereof. Examples of the additional active ingredients include, but are not limited to, antidepressants, anticonvulsants, antihypertensives, anxiolytics, calcium channel blockers, muscle relaxants, non-narcotic analgesics, opioid analgesics, anti-inflammatories, cox-2 inhibitors, immunomodulatory agents, immunosuppressive agents, corticosteroids, hyperbaric oxygen, or other therapeutics discussed herein (see, e.g., section 4.2).

Kits of the invention can further comprise devices that are used to administer the active ingredients. Examples of such devices include, but are not limited to, syringes, drip bags, patches, and inhalers.

Kits of the invention can further comprise pharmaceutically acceptable vehicles that can be used to administer one or more active ingredients. For example, if an active ingredient is provided in a solid form that must be reconstituted for parenteral administration, the kit can comprise a sealed container of a suitable vehicle in which the active ingredient can be dissolved to form a particulate-free sterile solution that is suitable for parenteral administration. Examples of pharmaceutically acceptable vehicles include, but are not limited to: Water for Injection USP; aqueous vehicles such as, but not limited to, Sodium Chloride Injection, Ringer's Injection, Dextrose Injection, Dextrose and Sodium Chloride Injection, and Lactated Ringer's Injection; water-miscible vehicles such as, but not limited to, ethyl alcohol, polyethylene glycol, and polypropylene glycol; and non-aqueous vehicles such as, but not limited to, corn oil, cottonseed oil, peanut oil, sesame oil, ethyl oleate, isopropyl myristate, and benzyl benzoate.

5. EXAMPLES

The following examples illustrate certain aspects of the invention, but do not limit its scope.

5.1 Pharmacology Studies

Pain is initiated by inflammatory reactions and sustained by the availability of inflammatory cytokines such as TNF-α TNF-α may play a pathological role in both nociceptive pain and neuropathic pain. One of biological effects exerted by immunomodulatory compounds is the reduction of synthesis of TNF-α Immunomodulatory compounds enhance the degradation of TNF-α mRNA. Increase of its expression in Schwann cells is shown in human painful neuropathies. Soluble TNF-α receptors are increased in the serum of patients with allodynia, as compared with neuropathy patients who do not report allodynia. The cytokine can induce ectopic activity in primary afferent nociceptors, and thus is a potential cause of hyperalgesia in neuropathic pain. One possible mechanism of this is that TNF-α can form active sodium ion channels in cells. Increased influx of sodium into nociceptors would dispose them toward ectopic discharge. The cytokine may play a pathological role if it is active at sites of nerve damage or dysfunction.

Without being limited by theory, when used pre-emptively, immunomodulatory compounds may reduce mechanical allodynia and thermal hyperalgesia in rats subjected to the chronic constriction injury model of neuropathic pain. In addition to reducing endoneurial TNF-α, the compounds may also cause a long-term increase in spinal cord dorsal horn met-enkephalin, an important antinociceptive neurotransmitter. Immunomodulatory compounds may also inhibit inflammatory hyperalgesia in rats and the writhing nociceptive response in mice.

Inhibitions of TNF-α production following LPS-stimulation of human PBMC and human whole blood by 3-(4-amino-1-oxo-1,3-dihydro-isoindol-2-yl)-piperidine-2,6-dione, 4-(amino)-2-(2,6-dioxo-(3-piperidyl))-isoindoline-1,3-dione and thalidomide were investigated in vitro. The $IC_{50}$'s of 4-(amino)-2-(2,6-dioxo-(3-piperidyl))-isoindoline-1,3-dione for inhibiting production of TNF-α following LPS-stimulation of PBMC and human whole blood were ~24 nM (6.55 ng/mL) and ~25 nM (6.83 ng/mL), respectively. The $IC_{50}$'s of 3-(4-amino-1-oxo-1,3-dihydro-isoindol-2-yl)-piperidine-2,6-dione for inhibiting production of TNF-α following LPS-stimulation of PBMC and human whole blood were ~100 nM (25.9 ng/mL) and ~480 nM (103.6 ng/mL), respectively. Thalidomide, in contrast, had an $IC_{50}$ of ~194 μM (50.1 μg/mL) for inhibiting production of TNF-α following LPS-stimulation of PBMC.

In vitro studies suggest a pharmacological activity profile for 3-(4-amino-1-oxo-1,3-dihydro-isoindol-2-yl)-piperidine-2,6-dione or 4-(amino)-2-(2,6-dioxo-(3-piperidyl))-isoindoline-1,3-dione is similar to, but 50 to 2,000 times more potent than, thalidomide. The pharmacological effects of 3-(4-amino-1-oxo-1,3-dihydro-isoindol-2-yl)-piperidine-2,6-dione or 4-(amino)-2-(2,6-dioxo-(3-piperidyl))-isoindoline-1,3-dione derive from its action as an inhibitor of cellular response to receptor-initiated trophic signals (e.g., IGF-1, VEGF, cyclooxygenase-2), and other activities. As a result, 3-(4-amino-1-oxo-1,3-dihydro-isoindol-2-yl)-piperidine-2,6-dione or 4-(amino)-2-(2,6-dioxo-(3-piperidyl))-isoindoline-1,3-dione suppresses the generation of inflammatory cytokines, down-regulates adhesion molecules and apoptosis inhibitory proteins (e.g., cFLIP, cIAP), promotes sensitivity to death-receptor initiated programmed cell death, and suppresses angiogenic response.

In addition, it has been shown that 3-(4-amino-1-oxo-1,3-dihydro-isoindol-2-yl)-piperidine-2,6-dione or 4-(amino)-2-(2,6-dioxo-(3-piperidyl))-isoindoline-1,3-dione is approximately 50 to 100 times more potent than thalidomide in stimulating the proliferation of T-cells following primary induction by T-cell receptor (TCR) activation. The compounds are also approximately 50 to 100 times more potent than thalidomide in augmenting the production of IL2 and IFN-γ following TCR activation of PBMC (IL2) or T-cells (IFN-γ). Further, the compounds exhibited dose-dependent inhibition of LPS-stimulated production of the pro-inflammatory cytokines TNF-α, IL1β and IL6 by PBMC while they increased production of the anti-inflammatory cytokine IL10.

5.2 Toxicology Studies

The effects of 3-(4-amino-1-oxo-1,3-dihydro-isoindol-2-yl)-piperidine-2,6-dione and 4-(amino)-2-(2,6-dioxo-(3-piperidyl))-isoindoline-1,3-dione on cardiovascular and respiratory function were investigated in anesthetized dogs. Two groups of Beagle dogs (2/sex/group) were used. One group received three doses of vehicle only and the other receives three ascending doses of 3-(4-amino-1-oxo-1,3-dihydro-isoindol-2-yl)-piperidine-2,6-dione or 4-(amino)-2-(2,6-dioxo-(3-piperidyl))-isoindoline-1,3-dione (2, 10, and 20 mg/kg). In all cases, doses of 3-(4-amino-1-oxo-1,3-dihydro-isoindol-2-yl)-piperidine-2,6-dione, 4-(amino)-2-(2,6-dioxo-(3-piperidyl))-isoindoline-1,3-dione or vehicle were successively administered via infusion through the jugular vein separated by intervals of at least 30 minutes.

The cardiovascular and respiratory changes induced by 3-(4-amino-1-oxo-1,3-dihydro-isoindol-2-yl)-piperidine-2,6-dione or 4-(amino)-2-(2,6-dioxo-(3-piperidyl))-isoindoline-1,3-dione were minimal at all doses when compared to the vehicle control group. The only statistically significant difference between the vehicle and treatment groups was a small increase in arterial blood pressure following administration of the low dose of 3-(4-amino-1-oxo-1,3-dihydro-isoindol-2-yl)-piperidine-2,6-dione or 4-(amino)-2-(2,6-dioxo-(3-piperidyl))-isoindoline-1,3-dione. This effect lasted approximately 15 minutes and was not seen at higher doses. Deviations in femoral blood flow, respiratory parameters, and Qtc interval were common to both the control and treated groups and were not considered treatment-related.

5.3 Studies Using Animal Pain Models

Immunomodulatory compounds can be tested for their ability to treat, prevent, manage and/or modify pain using any pain models well-known in the art. A variety of animal pain models are described in Hogan, Q., *Regional Anesthesia and Pain Medicine* 27(4):385-401 (2002), which is incorporated by reference herein in its entirety.

Examples of nociceptive pain models include a formalin test, hot-plate test and tail-flick test. Illustrative examples of the formalin test, hot-plate test and tail-flick test are set forth below.

The most commonly used neuropathic pain models are the Bennett, Selzer, and Chung models. Siddall, P. J. and Munglani, R., *Animal Models of Pain*, pp 377-384 in Bountra, C., Munglani, R., Schmidt, W. K., eds. *Pain: Current Understanding, Emerging Therapies and Novel Approaches to Drug Discover*, Marcel Dekker, Inc., New York, 2003. The Bennett and Selzer models are well-known and rapid to perform. The Chung model is robust for mechanical allodynia in most animals and is well characterized though complicated. These models represent a range of approaches to try and mimic some of the damage and dysfunction in clinical conditions. There are also animal models for diseases associated with pain, such as diabetic neuropathy or the new bone cancer and visceral pain models 5.3.1 Formalin Test for Measurement of Persistent Pain in Rats Animals are injected with an immunomodulatory compound or vehicle (controls) followed by the injection of formalin into the dorsal surface of the paw. The animal is observed to determine the number of times it flinches the injected paw over a period of 60 minutes. This model allows for the evaluation of anti-nociceptive drugs in the treatment of pain. Abbott, F. et al. *Pain* 60:91-102 (1995).

Animals are contained in shoe box cages for the duration of the experiment. Formalin (50 µl; 0.5%) is injected into the dorsal surface of the rear, right paw, by placing the needle (28.5 G) above the toes and below the ankle and inserting it beneath the surface of the skin. A timer is started immediately after the injection to mark the beginning of phase 1. The animal is observed for 10 minutes after injection and the number of times it flinches the injected paw are counted. Thirty minutes after the first formalin injection, phase 2 begins. Flinches are counted as in phase 1 for the next 20 minutes. An immunomodulatory compound is administered in an amount of from about 0.10 to about 150 mg/day by oral route up to 24 hrs prior to the formalin test. Animals are repeated in the order they are treated. Immediately following the completion of the test periods, animals are euthanized by $CO_2$ asphyxiation in accordance with IACUC guidelines.

Any animal experiencing unanticipated events at any time point throughout this study is evaluated for veterinary intervention. Any animal that cannot recover with standard veterinary care is euthanized immediately by $CO_2$ asphyxiation in accordance with IACUC guidelines.

5.3.2 Hot Plate Test for Measurement of Acute Pain in Rats

Animals are injected with an immunomodulatory compound or vehicle (controls) and then placed on the hot plate one at a time. Latency to respond to the heat stimulus is measured by the amount of time it takes for the animal to lick one of its paws. Malmberg, A. and Yaksh, T., *Pain* 60:83-90 (1995). This model allows for the evaluation of anti-nociceptive drugs in the treatment of pain. Langerman et al., *Pharmacol. Toxicol. Methods* 34:23-27 (1995).

Morphine treatment is used to determine the optimal hot-plate temperature. Doses of 8 to 10 mg/kg morphine (i.p.) provide a near-maximal anti-nociceptive response in acute pain assays. The apparatus is set to the temperature at which this type of anti-nociceptive response is observed with these doses of morphine (approximately 55° C.). An immunomodulatory compound is administered in an amount of from about 0.10 to about 150 mg/day by oral route up to 24 hrs prior to the hot-plate test. When the post-treatment time is elapsed, individual testing of animals is begun. A single animal is placed on the hot plate and a stopwatch or timer is immediately started. The animal is observed until it shows a nociceptive response (e.g., licks its paw) or until the cut-off time of 30 seconds is reached (to minimize tissue damage that can occur with prolonged exposure to a heated surface). The animal is removed from the hot-plate and its latency time to respond is recorded. For animals that do not respond prior to the cut-off time, the cut-off time will be recorded as their response time. Animals are repeated in the order they are treated. Animals are euthanized immediately following the experiment by $CO_2$ asphyxiation in accordance with IACUC guidelines.

Any animal experiencing unanticipated events at any time point throughout this study is evaluated for veterinary intervention. Any animal that cannot recover with standard veterinary care is euthanized immediately by $CO_2$ asphyxiation in accordance with IACUC guidelines.

5.3.3 Tail-Flick Test for Measurement of Acute Pain in Rats

Animals are injected with an immunomodulatory compound or vehicle (controls) and then a light beam is focused on the tail. Latency to respond to the stimulus is measured by the amount of time it takes for the animal to flick its tail. This model allows for the evaluation of anti-nociceptive drugs in the treatment of pain See, Langerman et al., *Pharmacol. Toxicol. Methods* 34:23-27 (1995).

An immunomodulatory compound is administered in an amount of from about 0.10 to about 150 mg/day by oral route up to 24 hrs prior to the tail flick test in accordance with the IACUC guidelines. When the post-treatment time is elapsed, individual testing of animals is begun. A single animal is placed on a tail flick apparatus exposing the ventral tail surface to a focused light beam. Response latency is the time from the application of the light until the tail is flicked. The animal is observed until it shows a nociceptive response (e.g., tail flick) or until the cut-off time of 10 seconds is reached (to minimize tissue damage that can occur with prolonged exposure to a heated surface). The animal is removed from the light source, its latency time to respond is recorded and then the animal is euthanized immediately by $CO_2$ asphyxiation in accordance with IACUC guidelines. The light beam intensity is adjusted to produce a baseline latency of 2.5-4 seconds. For animals that do not respond prior to the cut-off time, the cut-off time is recorded as their response time. Animals are repeated in the order they are treated.

Any animal experiencing unanticipated events at any time point throughout this study is evaluated for veterinary intervention. Any animal that cannot recover with standard veterinary care is euthanized immediately by $CO_2$ asphyxiation in accordance with IACUC guidelines.

5.3.4 Model For Topical Capsaicin-Induced Thermal Allodynia

A model particularly useful for thermal allodynia is the topical capsaicin-induced thermal allodynia model. Butelman, E. R. et al., *J. of Pharmacol. Exp. Therap.* 306:1106-1114 (2003). This model is a modification of the warm water tail withdrawal model. Ko, M. C. et al., *J. of Pharmacol. Exp. Therap.* 289:378-385 (1999). Briefly, monkeys sit in a custom made chair in a temperature-controlled room (20-22° C.). Their tails are shaved with standard clippers and tail withdrawal latencies are timed in 0.1 second increments up to a maximum of 20 seconds in both 38° C. and 42° C. water stimuli to provide a baseline. Following baseline determination, the tail is gently dried and degreased with an isopropyl alcohol pad. Approximately 15 minutes before use, capsaicin is dissolved in a vehicle composed of 70% ethanol and 30% sterile water for a final capsaicin concentration of either 0.0013 or 0.004 M. The solution (0.3 mL) is slowly injected onto a gauze patch, saturating the patch and avoiding overflow. Within 30 seconds of the capsaicin solution being added to the patch, capsaicin patch is fastened to the tail with tape. After 15 minutes, the patch is removed and tail withdrawal testing in both 38° C. and 42° C. water stimuli is performed as described above. Allodynia is detected as a decrease in tail withdrawal latency compared to the baseline measurements. To determine the ability of an immunomodulatory compound to decrease allodynia, a single dose of the compound is administered prior to (e.g. 15 minutes prior, 30 minutes prior, 60 minutes prior or 90 minutes prior) the application of the capsaicin patch. Alternatively, the allodynia reversal properties of an immunomodulatory compound can be determined by administering a single dose of the compound after application of the capsaicin patch (e.g., immediately after, 30 minutes after, 60 minutes after or 90 minutes after).

The capsaicin model may be appropriate for agents to be used to treat hyperalgesia and allodynia (e.g. vanilloid receptor 1 (VR1) antagonists and AMPA antagonists), whereas UV skin burn may be appropriate for bradykinin B1 receptor antagonists, cannabinoid agonists, and VR1 antagonists. Clinical applications of the capsaicin model have supported the antihyperalgesic effects of several clinically used drugs such as opioids, local anesthetics, ketamine and gabapentin. Visceral models have, as yet, unknown potential as hyperalgesic models and require validation.

5.4 Clinical Studies in Pain Patients

Immunomodulatory compounds such as 4-(amino)-2-(2,6-dioxo(3-piperidyl))-isoindoline-1,3-dione and 3-(4-amino-1-oxo-1,3-dihydro-isoindol-2-yl)-piperidine-2,6-dione are administered in an amount of 0.1 to 25 mg per day to patients with pain syndromes for three to six months. A baseline evaluation is performed for the effect of the drug treatment on pain intensity, impact of pain on activities of daily living, and consumption of other pain medications.

In a specific embodiment, clinical studies are performed in pain patients who have upper extremity CRPS that has not responded to conventional physical therapy and has been present for at least one year. In the early course of their diseases, patients have clear evidence of autonomic dysfunction with formal autonomic testing (Quantitative sudomotor axon reflex test (QSART), resting sweat output, and thermography). If this is unavailable, documentation of clinical signs indicates autonomic dysfunction (changes in hydration, temperature, skin, nail or hair growth) along with symptoms of allodynia and swelling. Patients receive continuous treatment with 3-(4-amino-1-oxo-1,3-dihydro-isoindol-2-yl)-piperidine-2,6-dione at a oral dose of 10 to 25 mg daily. Responses are assessed using standard pain scales, e.g., Numeric Pain Scale Assessment (VAS) for pain, quality of life using the McGill Index and objective signs in clinical examination such as a visible reduction of swelling, sweating, discolorations in skin color, temperature changes, changes in skin, hair and nail growth, and fine motor movements. Treatment with 10 mg as a continuous oral daily dose is well-tolerated. The study in CRPS patients treated with the immunomodulatory compounds suggests that the drugs have analgesic benefit in this disease.

Embodiments of the invention described herein are only a sampling of the scope of the invention. The full scope of the invention is better understood with reference to the attached claims.

What is claimed is:

1. A method of treating, modifying or managing radiculopathy, which comprises administering to a patient having radiculopathy a therapeutically effective amount of 1-oxo-2-(2,6-dioxopiperidin-3-yl)-4-aminoisoindoline of the formula,

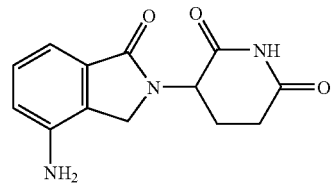

or a pharmaceutically acceptable salt, solvate or stereoisomer thereof.

2. The method of claim 1, wherein the compound is 1-oxo-2-(2,6-dioxopiperidin-3-yl)-4-aminoisoindoline.

3. The method of claim 1, wherein the compound is a pharmaceutically acceptable salt.

4. The method of claim 1, wherein the compound is a pharmaceutically acceptable solvate.

5. The method of claim 1, wherein the compound is a pharmaceutically acceptable stereoisomer.

6. The method of claim 5, wherein the stereoisomer is an enantiomerically pure R isomer.

7. The method of claim 5, wherein the stereoisomer is an enantiomerically pure S isomer.

8. The method of claim 1, which further comprises administering a therapeutically effective amount of a second active agent.

9. The method of claim 8, wherein the second active agent is an antidepressant, antihypertensive, anxiolytic, calcium channel blocker, alpha-adrenergic receptor agonist, alpha-adrenergic receptor antagonist, ketamine, anesthetic, muscle relaxant, non-narcotic analgesic, opioid analgesic, anti-inflammatory agent, immunomodulatory agent, immunosuppressive agent, corticosteroid, anticonvulsant, cox-2 inhibitor, hyperbaric oxygen, or a combination thereof.

10. The method of claim 8, wherein the second active agent is salicylic acid acetate, celecoxib, ketamine, gabapentin, carbamazepine, oxcarbazepine, phenyloin, sodium valproate, prednisone, nifedipine, clonidine, oxycodone, meperidine, morphine sulfate, hydromorphone, fentanyl, acetaminophen, ibuprofen, naproxen sodium, griseofulvin, amitriptyline, imipramine or doxepin.

11. The method of claim 1, wherein the compound is administered orally.

12. The method of claim 11, wherein the compound is administered in the form of a capsule or tablet.

13. The method of claim 1, wherein the compound is administered in an amount of from about 0.1 to about 150 mg per day.

14. The method of claim 1, wherein the compound is administered in an amount of from about 5 to about 50 mg per day.

15. The method of claim 14, wherein the compound is administered in an amount of about 5 to about 25 mg per day.

16. The method of claim 14, wherein the compound is administered in an amount of about 25 mg per day.

17. The method of claim 14, wherein the compound is administered in an amount of about 10 mg per day.

* * * * *